US006989400B2

(12) United States Patent
Tidmarsh

(10) Patent No.: US 6,989,400 B2
(45) Date of Patent: Jan. 24, 2006

(54) TREATMENT OF BENIGN PROSTATIC HYPERPLASIA

(75) Inventor: George Tidmarsh, Portola Valley, CA (US)

(73) Assignee: Threshold Pharmaceuticals, Inc., Redwood City, CA (US)

( * ) Notice: Subject to any disclaimer, the term of this patent is extended or adjusted under 35 U.S.C. 154(b) by 82 days.

(21) Appl. No.: 10/759,337

(22) Filed: Jan. 16, 2004

(65) Prior Publication Data

US 2004/0167196 A1 Aug. 26, 2004

Related U.S. Application Data

(60) Provisional application No. 60/496,163, filed on Aug. 18, 2003, provisional application No. 60/488,265, filed on Jul. 18, 2003, provisional application No. 60/472,907, filed on May 22, 2003, provisional application No. 60/460,012, filed on Apr. 2, 2003, provisional application No. 60/458,846, filed on Mar. 28, 2003, provisional application No. 60/458,665, filed on Mar. 28, 2003, provisional application No. 60/458,663, filed on Mar. 28, 2003, provisional application No. 60/442,344, filed on Jan. 23, 2003, provisional application No. 60/441,110, filed on Jan. 17, 2003.

(51) Int. Cl.
A61K 31/415 (2006.01)

(52) U.S. Cl. .................................................. 514/403
(58) Field of Classification Search ................. 514/403
See application file for complete search history.

(56) References Cited

U.S. PATENT DOCUMENTS

| 3,895,026 | A |   | 7/1975 | Palazzo et al. |
| 4,684,627 | A |   | 8/1987 | Leveen et al. |
| 4,840,939 | A |   | 6/1989 | Leveen et al. |
| 5,260,327 | A | * | 11/1993 | Kim et al. .................. 514/405 |
| 5,827,887 | A |   | 10/1998 | Gourvest et al. |
| 6,001,865 | A | * | 12/1999 | Silvestrini et al. .......... 514/403 |
| 6,319,517 | B1 |   | 11/2001 | Cavallo et al. |
| 6,337,087 | B1 |   | 1/2002 | Cavallo et al. |
| 6,428,968 | B1 | * | 8/2002 | Molnar-Kimber et al. . 435/7.23 |
| 6,482,802 | B1 | * | 11/2002 | Hu et al. ...................... 514/39 |

FOREIGN PATENT DOCUMENTS

| CA | 2206198 | 5/1997 |
| IE | 54256 | 8/1989 |
| WO | WO 96/40142 A1 | 12/1996 |
| WO | WO 97/14670 A1 | 4/1997 |
| WO | WO 98/10781 A1 | 3/1998 |
| WO | WO 2004/064735 A2 | 8/2004 |
| WO | WO 2004/064736 A2 | 8/2004 |

OTHER PUBLICATIONS

Isaacs et al., Prostate, Supplement, (1989), 2, 33-50 (Abstract Only, Medline Acc. No. 90148756).*
Kirby, Urology, (Nov. 1, 2000), 56 (5 Suppl. 1), 3-6 (Abstract Only, Medline Acc. No. 2001035623).*
Harrison's Principles of Internal Medicine, 13$^{th}$ ed. , vol. 2, published 1994 by McGraw-Hill, Inc. (NY), pp. 18-62-1865.*
Stedman's Medical Dictionary, 25$^{th}$ Edition, published 1990, by Williams & Wilkins, p. 65, "analog".*
Belzacq et al., Oncogene, 2001, 7579-87, 20.
Belzacq et al., Biochimie, 2002, 167-76, 84.
Berruti et al., J. Clin. Oncol., 2002, 4150-9, 20(20).
Besner et al., Oncology, 1984, 48-52, 41(supp. 1).
Besner et al., Drug Metabolism Rev., 1997, 219-234, 29 (1&2).
Bunn, J. Clin. Onc., 2002, 23-33, 20(18).
Calabresi et al., Sem. Onc., 1991, 66-72, 18(2).
Cionini, Sem. Onc., 1991, 49-52, 18(2) Suppl. 4.
Comella et al., J. Clin. Onc., 1999, 1526-34, 17(5).
Corsi et al., J. Med. Chem., 1976, 778-783, 19(6).
Costello & Franklin, Oncology, 2000, 269-282, 59.
Costello et al., J. Inorg. Biochem., 2000, 161-165, 78.
Cuna et al., Apr., Sem. Onc., 1991, 18-22, 18 (2 supp. 4).
De Lena et al., Eur. J. Can., 2001, 364-8, 37.
De Lena et al., J. Clin. Onc., 1997, 3208-13, 15(10).
Floridi et al., Arch. Biochem. Biophys., 1983, 73-83, 226(1).
Floridi et al., Can. Res., Nov., 1981, 4661-6, 41.
Gatzemeier et al., Sem. Onc., 1991, 42-8, 18(2) Suppl. 4.
Grima et al., Biol. Reprod., 2001, 1500-8, 64.
Heywood et al., Chemotherapy, 1981, 91-97, 27 (Suppl. 2).
Ianniello et al., 1996, Cancer, 63-9, 78(1).
Lobl et al., Chemotherapy, 1981, 61-76, 27 (Suppl. 2).
Mansi et al., Br. J. Cancer, 1991, 593-7, 64.
Muntzing et al., J. Med. Primatol., 1975, 245-251, 4.
Orlandi et al., Int. J. Can., 1998, 377-84, 78.
Orlandi et al., Anticancer Res., 1994, 1161-4, 14.
Pacini et al., Eur. J. Cancer, 2000, 966-75, 36.
Paggi et al., Ann. NY Acad. Sci., 1988, 358-60, 551.
Portalone et al., Tumori, 1999, 239-42, 85.
Possinger et al., Sem. Onc., 1991, 58-61, 18(2) Suppl. 4.
Price et al., Cancer Chemother. Phramacol., 1996, 129-135, 38.
Privitera et al., Radiother. Onc., 1987, 285-90, 10.
Ravagnan et al., Oncogene, 1999, 2537-46, 18.
Rosso et al., Sem. Onc., 1991, 62-5, 18(2) Suppl. 4.
Rotin et al., Int. J. Radiation Oncology Biol. Phys., 1984, 1595-8, 10.
Savini et al., Breast. Can. Res. Treat., 1992, 27-34, 24.

(Continued)

Primary Examiner—Raymond J. Henley, III
(74) Attorney, Agent, or Firm—Ted Apple; Vandana Date; Kevin R. Kaster

(57) ABSTRACT

A method for treatment or prophylaxis of benign prostatic hyperplasia by administration of lonidamine or a lonidamine analog is provided. Also provided are unit dosage forms of lonidamine or an analog, useful for such treatment and prophylaxis.

24 Claims, 8 Drawing Sheets

OTHER PUBLICATIONS

Scarantino et al., Sem. Onc., 1991, 28-32, 18(2) Suppl. 4.
Schiffer et al., Sem. Onc., 1991, 38-41, 18(2) Suppl. 4.
Silvestrini, Sem. Onc., 1991, 2-6, 18(2) Suppl. 4.
Segre et al., Chemotherapy, 1981, 77-84, 27 (Suppl. 2).
Teicher et al., Sem. Onc., 1991, 7-10, 18(2) Suppl. 4.
Teicher et al., Eur. J. Cancer, 1994, 1411-3, 30A(10).
Vieira et al., Cell Death and Differentiation, 2000, 1146-1154, 7.
Zaniboni et al., Tumori, 1995, 435-7, 81.
Isaacs et al., "Etiology and disease process of benign prostatic hyperplasia" *Prostate Suppl.*, 2:33-50 (1989).
Hudson et al., "Proliferative heterogeneity in the human prostate: evidence for epithelial stem cells" *Lab Invest.*, 80:1243-1250 (2000).
Collins et al., "Benign prostatic stromal cells are regualted by basic fibroblast growth factor and transforming growth factor-beta 1" *J Endocrinol.*, 151:315-322 (1996).
Giri et al., "Interleukin-8 is a parascrine inducer of fibroblast growth factor 2, a stromal and epithelial growth factor in benign prostatic hyperplasia" *Am. J Pathol.*, 159:139-147 (2001).
Castro et al., "Interleukin-8 expression is increased in senescent prostatic epithelial cells and promotes the development of benign prostatic hyperplasia" *Prostate*, 60:153-159 (2004).
Boccardo et al., "Phase II study with Ionidamine in the treatment of hormone-refractory prostatic cancer patients" *Tumori*, 78:137-139 (1992).
Dudak et al., "Enhancement of radiation response of prostatic carcinoma by Ionidamine" *Anticancer Res.*, 16: 3665-3671 (1996).
Bloch et al., "Enhancement of hyperthermic toxicity by Ionidamine in the Dunning R3327G rat prostatic adenocarcinoma" *Prostate*, 24:131-138 (1994).
Benz et al., "Lactic dehydrogenase isozymes, 31P magnetic resonance spectroscopy, and in vitro antimitochondrial tumor toxicity with gossypol and rhodamine-123," *J Clin Invest.* 79:517-523. (1987).
Eri et al., "Effects on the endocrine system of long-term treatment with the luteinizing hormone-releasing hormone agonist leuprolide in patients with benign prostatic hyperplasia" *Scandinavian Journal of Clinical and Laboratory Investigation*, 56: 319-325 (1996).
International Search Report and Written Opinion for PCT/US2004/001141 (WO 2004/064735) (Sep. 22, 2004).
International Search Report and Written Opinion for PCT/US2004/001146 (WO 2004/064736) (Mar. 1, 2005).
Lobl, 1979, "1-(2,4-Dicholorobenzyl)-1H-Indazole-3Carboxylic Acid (DICA), and Exfoliative Antispermatogenic Agent in the Rat" *Arch Andrology* 2:353-63.
Shidaifat et al, 1997, "Gossypol arrests human benign prostatic hyperplastic cell growth at G0/G1 phase of the cell cycle" *Anticancer Res.* 17:1003-9.
Chang, 1997, "Gossypol induces spermidine/spermine N1-acetyltransferase in canine prostate epithelial cells" *Biochem Biophys Res Commun.* 231:383-8.

* cited by examiner

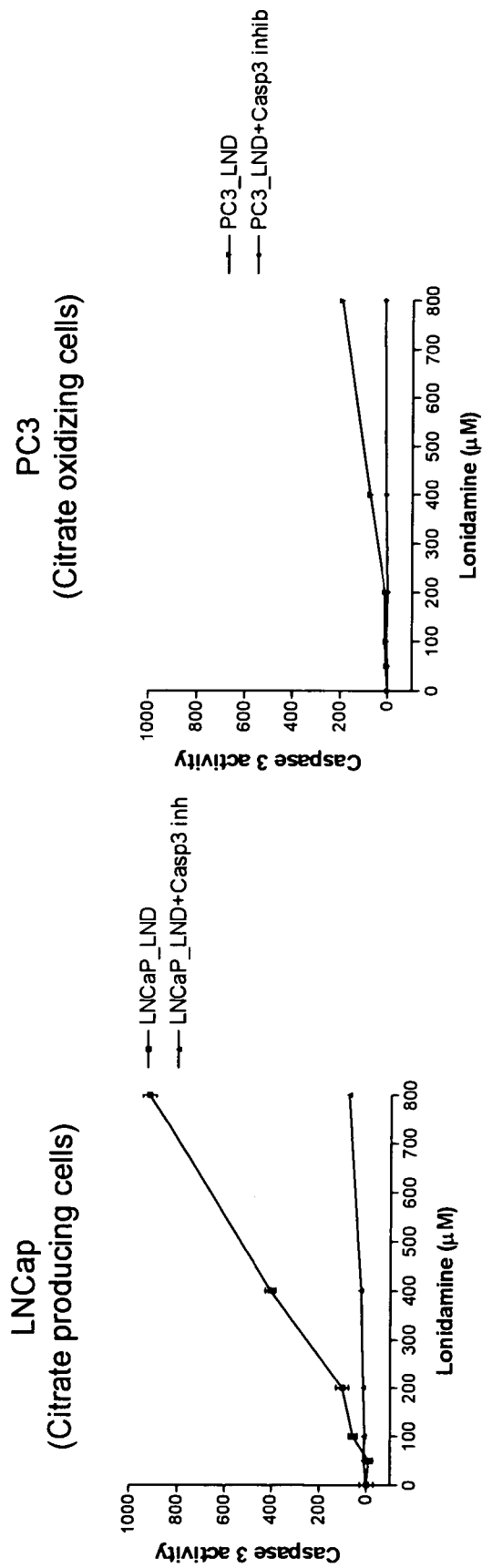

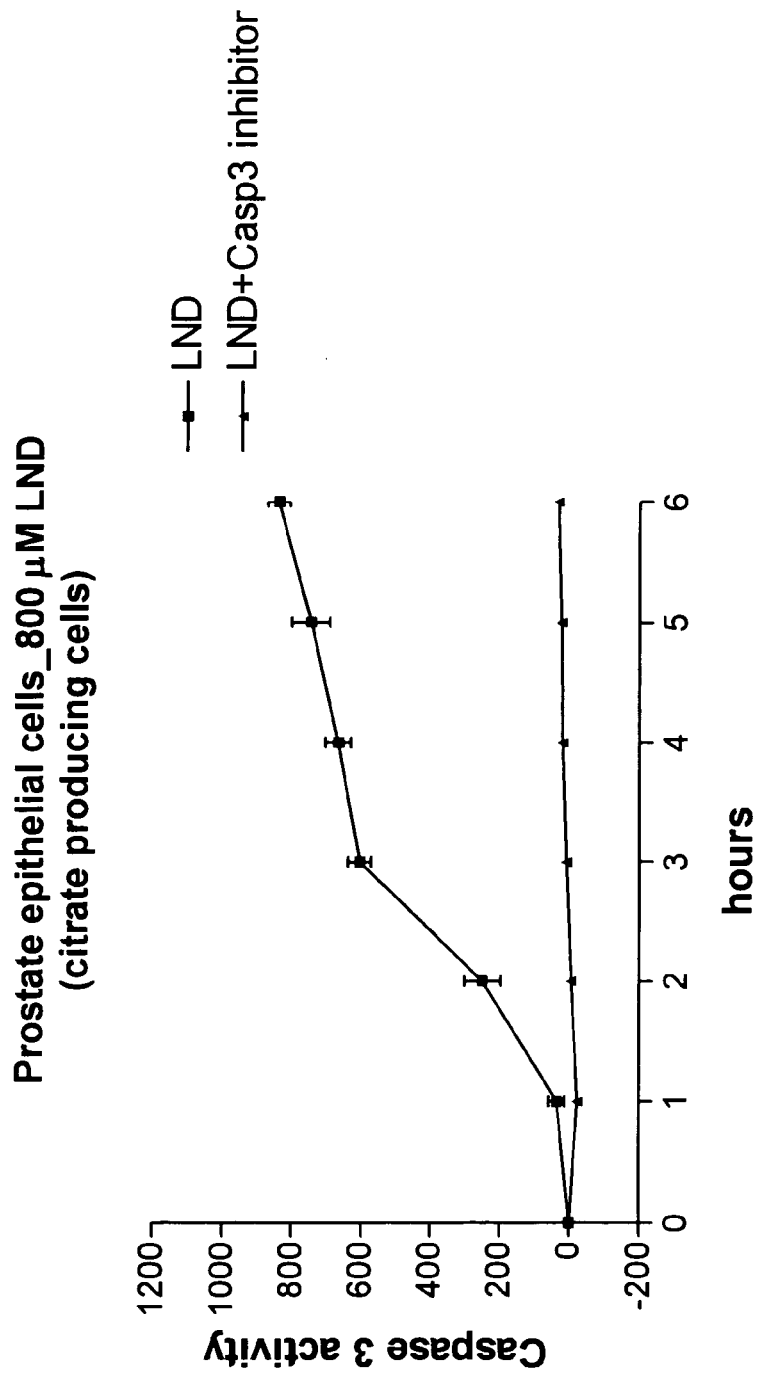

TREATMENT OF BENIGN PROSTATIC HYPERPLASIA

CROSS-REFERENCE TO RELATED APPLICATIONS

This application claims benefit of U.S. provisional application Nos. 60/496,163 (filed 18 Aug. 2003), 60/488,265 (filed Jul. 18, 2003); 60/472,907 (filed 22 May 2003), 60/460,012 (filed 2 Apr. 2003), 60/458,846 (filed 28 Mar. 2003), 60/458,665 (filed 28 Mar. 2003), 60/458,663 (filed 28 Mar. 2003), 60/442,344 (filed 23 Jan. 2003), and 60/441,110 (filed 17 Jan. 2003), each of which is incorporated herein by reference in its entirety for all purposes.

FIELD OF THE INVENTION

The invention relates to treatment and prevention of benign prostatic hyperplasia, and has application in the field of medicine and related fields, including chemistry, medicinal chemistry, and molecular biology.

BACKGROUND OF THE INVENTION

Benign Prostatic Hyperplasia (BPH), a disease in which prostate epithelial cells grow abnormally and block urine flow, afflicts more than 10 million adult males in the United States, and many millions more throughout the rest of the world. Until relatively recently, surgical intervention was the only treatment of the disease, and even today, surgery is the treatment of last resort, almost inevitably relied upon when other treatments are not, or cease to be, effective. Prostate surgery and recovery therefrom is painful, and the surgery itself may not be effective and poses the risk of serious side effects. For a recent review, see Barry, 2001 (full citations are provided below).

Only two classes of drugs are currently available to treat the symptoms of BPH. One class includes compounds that inhibit production of the active form of testosterone (dihyrdotestosterone or DHT). Use of drugs in this class can cause a loss of libido and loss of muscle mass and tone in males and is associated with an increased occurrence of high grade prostate cancer. In addition, this therapy is limited by the very long delay (months) between first administering the drug and significant reduction in prostate size in the patient. The second class of currently used drugs for BPH, alpha adrenergic blockers, acts by relaxing the smooth muscles, allowing urine to pass through the urethra more freely. While this class of drugs reduces symptoms more rapidly than the first, it does not reduce the size of the prostate or prevent it from growing larger, which can lead to eventual surgical intervention.

Thus, there is a significant, unmet need for drugs that can treat the underlying disease condition of BPH without serious side effects. The present invention meets that need.

SUMMARY OF THE INVENTION

The invention provides methods and compositions for treating BPH in a human subject by administration of lonidamine or a lonidamine analog to the subject. Pharmaceutical compositions useful for treatment of BPH, including sustained release formulations, are also provided. In one embodiment, the formulation is orally administered and permits once-a-day dosing of a therapeutically effective dose of the compound.

BRIEF DESCRIPTION OF THE FIGURES

FIG. 2A shows an assay using a nuclear extract. FIGS. 2B and 2C show an assay using a whole cell extract.

FIGS. 3A and 3C show an assay using a nuclear extract. FIG. 3B shows an assay using a whole cell extract.

FIG. 4 shows lonidamine-induced apoptosis in LNCaP (FIG. 4A) and PC-3 (FIG. 4B) cells.

FIG. 5 shows lonidamine-induced apoptosis in prostate epithelial cells.

DETAILED DESCRIPTION OF THE INVENTION

1. Definitions

Figure 1:
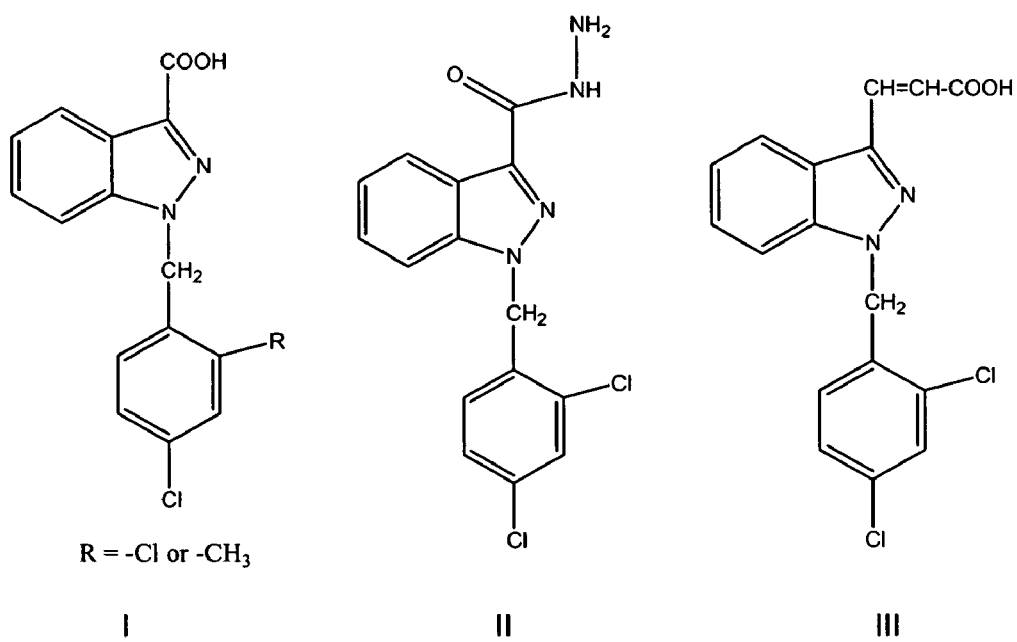
FIG. 1 shows structures for lonidamine (I, R=Cl), tolnidamine (I, R=CH$_3$), AF-2364 (II) and AF-2785 (III).

The following definitions are provided to assist the reader. Unless otherwise defined, all terms of art, notations and other scientific or medical terms or terminology used herein are intended to have the meanings commonly understood by those of skill in the chemical and medical arts. In some cases, terms with commonly understood meanings are defined herein for clarity and/or for ready reference, and the inclusion of such definitions herein should not necessarily be construed to represent a substantial difference over the definition of the term as generally understood in the art.

As used herein, "treating" a condition or patient refers to taking steps to obtain beneficial or desired results, including clinical results. For purposes of this invention, beneficial or desired clinical results include, but are not limited to, alleviation or amelioration of one or more symptoms of BPH, diminishment of extent of disease, delay or slowing of disease progression, amelioration, palliation or stabilization of the disease state, and other beneficial results described below.

As used herein, "reduction" of a symptom or symptoms (and grammatical equivalents of this phrase) means decreasing of the severity or frequency of the symptom(s), or elimination of the symptom(s).

As used herein, "administering" or "administration of" a drug to a subject (and grammatical equivalents of this phrase) includes both direct administration, including self-administration, and indirect administration, including the act of prescribing a drug. For example, as used herein, a physician who instructs a patient to self-administer a drug and/or provides a patient with a prescription for a drug is administering the drug to the patient.

As used herein, a "manifestation" of BPH refers to a symptom, sign, anatomical state (e.g., prostate size), physiological state (e.g., PSA level), or report (e.g., AUASI score) characteristic of a subject with BPH.

As used herein, a "therapeutically effective amount" of a drug is an amount of a drug that, when administered to a subject with BPH, will have the intended therapeutic effect, e.g., alleviation, amelioration, palliation or elimination of one or more manifestations of BPH in the subject. The full therapeutic effect does not necessarily occur by administration of one dose, and may occur only after administration of a series of doses. Thus, a therapeutically effective amount may be administered in one or more administrations.

As used herein, a "prophylactically effective amount" of a drug is an amount of a drug that, when administered to a subject, will have the intended prophylactic effect, e.g., preventing or delaying the onset (or reoccurrence) of disease or symptoms, or reducing the likelihood of the onset (or reoccurrence) of disease or symptoms. The full prophylactic effect does not necessarily occur by administration of one dose, and may occur only after administration of a series of doses. Thus, a prophylactically effective amount may be administered in one or more administrations.

As used herein, "TID" and "QD" have their ordinary meanings of "three times a day" and "once daily," respectively.

As used herein, "alkyl" refers to a monovalent alkane (hydrocarbon) derived radical containing from 1 to 15 carbon atoms. It may be straight, branched or cyclic and may be unsubstituted or substituted with substituent groups including but not limited to hydroxyl, halide, alkoxyl, and nitrile. Alkoxy groups that can be used include but are not limited to methooxy. Illustrative straight or branched alkyl groups include methyl, ethyl, propyl, isopropyl, butyl and t-butyl.

As used herein, "aryl" refers to moieties that include one or more monocyclic or fused ring aromatic systems. Such moieties include any moiety that includes one or more monocyclic or bicyclic fused ring aromatic systems, including but not limited to phenyl and naphthyl. Aryl groups may be unsubstituted or substituted with substituent groups as listed for the particular substituted aryl.

As used herein, "heteroaryl" refers to monocyclic aromatic groups having 5 or 6 ring atoms, or fused ring bicyclic aromatic groups having 8 to 10 atoms, in which the ring atoms are C, O, S, SO, $SO_2$, or N and at least one of the ring atoms is a heteroatom, i.e., O, S, SO, $SO_2$, or N. Heteroaryl groups may be unsubstituted or substituted with substituent groups as listed for the particular substituted heteroaryl. Examples of monocyclic aromatic heteroaryl groups include but are not limited to pyridyl. Examples of bicyclic fused ring heteroaryl groups include but are not limited to indazolyl, pyrrolopyrymidinyl, indolizinyl, pyrazolopyridinyl, triazolopyridinyl, pyrazolopyrimidinyl, triazolopyrimidinyl, pyrrolotriazinyl, pyrazolotriazinyl, triazolotriazinyl, pyrazolotetrazinyl, hexaaza-indenly, and heptaaza-indenyl. Unless indicated otherwise, the arrangement of the hetero atoms within the ring may be any arrangement allowed by the bonding characteristics of the constituent ring atoms.

As used herein, the terms "heterocycloalkyl" and "heterocyclyl" refer to a monocyclic or fused ring multicyclic cycloalkyl group at least a portion of which is not aromatic and in which one or more of the carbon atoms in the ring system is replaced by a heteroatom selected from O, S, SO, $SO_2$, or N. Examples of heterocyclyl groups include but are not limited to piperidinyl, morpholinyl, pyrrolidinyl, tetrahydrofuranyl, tetrahydroimidazo [4,5-c]pyridinyl, imidazolinyl, piperazinyl, pyrrolidine-2-onyl, and piperidin-2-onyl.

As used herein, "cycloalkyl" refer to a monocyclic or fused ring multicyclic group at least a portion of which is not aromatic and in which the ring atoms are carbon.

As used herein "heterocycloalkenyl" refers to a monocyclic or fused ring multicyclic group in which one or more of the carbon ring atoms is replaced by a hetero atom, the ring system is at least partially not aromatic, and the ring system includes at least one carbon-carbon double bond.

2. Benign Prostatic Hyperplasia and the Effects of Lonidamine and Lonidamine Analogs The present invention provides compositions and methods useful in the treatment of benign prostatic hyperplasia (BPH). In particular, the invention relates to the use of lonidamine (LND) for the treatment or prevention of BPH. Additionally, the invention relates to the use of lonidamine analogs for the treatment or prevention of BPH. To aid in understanding the invention, a brief discussion of BPH (also referred to as benign prostatic hypertrophy) and the properties of lonidamine and its bioactive analogs is provided below.

BPH involves overgrowth (hyperplasia) of cells in the prostate, resulting in enlargement of the prostate and leading to lower urinary tract symptoms and disease. The prostate gland contains secretory epithelial cells in a stroma of connective tissue and smooth muscle (see Barry, 2003, for a more detailed description of prostate anatomy), and BPH involves hyperplasia of the epithelial component. The secretory epithelial component in the normal prostate is remarkable in that the level of zinc in this tissue is very high compared to other normal tissues. A consequence of the high zinc levels is that, through a mechanism involving zinc inhibition of the enzyme m-aconitase, the generation of energy via the tricarboxylic acid (TCA) cycle and oxidative phosphorylation is substantially reduced in the secretory epithelium, making this tissue far more dependent than other organs and tissues upon glycolysis as an energy source. The zinc inhibition of m-aconitase, a key enzyme in the TCA cycle, results in at least a substantial reduction in, and perhaps a near complete blockade of, the TCA cycle in prostate epithelial cells. Another physiological result of the zinc-based inhibition of maconitase is the diversion of citrate from the TCA cycle, enabling the prostate to secrete large quantities of citrate, used by the sperm as an energy source, into the seminal fluid. See, generally, Costello, 1999; Costello et al., 2000; Costello and Franklin, 2000.

As other normal cells in the body do not accumulate zinc to a level inhibitory to the metabolism of citrate, prostate epithelial cells are uniquely dependent on glycolysis (anaerobic metabolism). The present invention relates in part to the discovery of these cells' susceptibility to the drug lonidamine, which allows lonidamine to be administered, as described herein, to treat or prevent BPH in humans. Lonidamine is the generic name for 1-(2,4-dichlorobenzyl)-1H-indazole-3-carboxylic acid, and has also been referred to in the medical literature as 1-[(2,4-dichlorophenyl)methyl]-1H-indazole-3-carboxylic acid, AF1890, diclondazolic acid (DICA), and Doridamina™. See FIG. 1. Lonidamine was first identified as an antispermatogenic agent, and subsequently used in the treatment of breast, cervical, lung and prostate cancers, in a few countries in Europe. See Silvestrini, 1981; Gatto et al., 2002. The mechanisms of action of lonidamine in spermatogenesis and cancer may not be completely understood. However, it has been suggested that lonidamine's anticancer properties result at least in part from a lonidamine-mediated disruption of the mitochondrial membrane, resulting in reduced activity of mitochondrially-bound hexokinase and interference with ATP production by the glycolytic pathway and oxidative phosphorylation. See, Floridi et al., 1981, Fanciulli et al., 1996, and references numbered 15–22 therein; and Gatto, 2002. Also see Kaplan, 2000. Without intending to be bound by a specific mechanism for the effects of lonidamine in benign prostatic hyperplasia, it is believed that lonidamine inhibits glycolysis and/or impairs the already diminished mitochondrial function in prostate epithelial cells, starving these cells, relative to the normal cells in the body, of energy. Without intending to be bound by a specific mechanism, it is believed that, due to this energy deprivation, enough of the hyperplastic, epithelial cells are destroyed or otherwise reduced in size to reduce the size of the prostate and thereby relieve the condition and its clinical consequences.

Accordingly, administration of lonidamine to a human subject diagnosed with, or exhibiting symptoms of, BPH provides benefits such as reduction of severity or frequency of one or more symptoms, reduction in prostate size or rate of enlargement, improvement in perceived quality of life, and reversion of other manifestations of BPH toward a more normal state. Further, administration of lonidamine to a human subject in need of prophylaxis for BPH provides benefits such as a reduction in likelihood that BPH will appear, reappear or progress in the subject. Still further, administration of a lonidamine analog to a human subject is similarly effective for treatment and prophylaxis of BPH. In another embodiment, administration of lonidamine or its analogs to a human subject as described herein can be efficacious in the treatment of acute urinary retention. These and other aspects of the invention are discussed in greater detail below. Section 3, below, describes certain lonidamine analogs useful for treatment and prophylaxis of BPH. Section 4 relates to synthesis and forms of lonidamine and lonidamine analogs. Section 5 describes patient populations for whom administration of lonidamine and lonidamine analogs provides benefit. Section 6 describes methods of administration of lonidamine (e.g., dose, route, schedule and duration of administration). Section 7 describes combination therapies in which lonidamine or an analog is administered in combination with another drug or therapy. Section 8 describes exemplary dosage forms. Section 9 provides examples of the use and effects of lonidamine. The description below is organized into sections for convenience only, and disclosure found in any organizational section is applicable to any aspect of the invention.

3. Lonidamine Analogs

As noted above, in addition to lonidamine, a variety of compounds related to lonidamine are useful for the treatment and prevention of BPH. Useful compounds are generally structurally similar to, are bioisosteres of, or are pharmacophores of lonidamine, as described below, and have biological activity(s) similar to those of lonidamine, as also discussed below. Such compounds can be referred as "bioactive lonidamine analogs," "lonidamine analogs," or, in some cases, simply, "analogs."

Structural characteristics of lonidamine analogs. Based, in part, on the structure of lonidamine and related compounds known to have pharmaceutical activities similar to that of lonidamine, certain lonidamine analogs, including novel analogs provided by the present invention, suitable for use in treatment or prophalaxis of BPH are described by the formula,

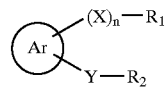

where $R_1$, $R_2$, X, Y, n and

are defined below:

$R_1$ represents —COOH or a derivative or bioisostere of the —COOH group. $R_1$ is usually selected from an acid group of formula —COOH; an amide of formula —CONR$_3$R$_4$, where $R_3$ and $R_4$ may be independently alkyl or hydrogen, with hydrogen preferred; a hydrazide of formula —CONHNR$_6$R$_7$, where $R_6$ and $R_7$ are usually —H or —CH$_3$; a substituted ester of formula —COOR$_5$, with $R_5$ being a residue easily hydrolyzed in the subject after administration and generally a straight chain or branched chain alkyl group substituted with one or more hydroxyl groups, more usually a straight chain or branched chain methyl, ethyl, or propyl group substituted with one or more hydroxyl groups, more usually still an ethyl group substituted with one hydroxyl group or a straight chain or branched chain propyl group substituted with two hydroxyl groups, and most usually —CH$_2$CH$_2$OH, —CH$_2$CH(OH)CH$_2$OH, or —CH$_2$(CH$_2$OH)$_2$. $R_1$ may also be the carboxylate anion of formula —COO$^-$, in which case the lonidamine or lonidamine analog will be associated with a counter ion, $Z^+$, where $Z^+$ is a pharmaceutically acceptable cation.

$R_2$ represents a substituted or unsubstituted aryl or heteroaryl group. Usually, $R_2$ is a substituted aryl group; more usually, a substituted phenyl group; more usually still, a phenyl group substituted by one, two, or three substituents independently selected from halo and alkyl substituents, particularly —Cl, —Br, —I, CF$_3$ and —CH$_3$ substituents. When $R_2$ is a substituted phenyl group, $R_2$ is usually —Cl, —Br, —I, CF$_3$ or —CH$_3$, monosubstituted phenyl, substituted at the 2, 3, or 4 position; dichloro, dibromo, dimethyl, or chloro and methyl disubstituted phenyl, substituted at the 2 and 3 or 2 and 4 positions; or 2, 4, 5 trichlophenyl. When $R_2$ is a substituted phenyl group, $R_2$ is more usually 2,4-dichlorophenyl or 4-chloro-2-methylphenyl.

X represents a straight chain or branched chain, saturated or unsaturated hydrocarbon linkage group. When X is a saturated hydrocarbon linkage group, X is usually a straight chain linkage group and usually X has the formula —(CH$_2$)$_p$—, with p equal to 1, 2, or 3. When X is a saturated hydrocarbon linkage group, X is most usually a methylene group, —(CH$_2$)—. When X is an unsaturated hydrocarbon linkage group, X is usually a straight chain linkage group, most usually —(CH=CH)—.

Y represents a moiety of formula —CHR$_7$—, where $R_7$ is hydrogen or a straight chain or branched chain alkyl group, more usually $R_7$ is hydrogen or or a straight chain alkyl group, more usually still $R_7$ is hydrogen, methyl, ethyl, or n-propyl, more usually still $R_7$ is hydrogen or methyl, and most usually $R_7$ is hydrogen (i.e., Y is most usually —CH$_2$—).

n is zero or, most usually, one.

is a core ring system that may generally be an aryl, heteroaryl, cycloalkyl or heterocyclyl ring system. The Ar core ring system usually includes 2 fused rings. The fused rings may generally be 4-, 5-, 6-, 7-, or 8-membered rings, more usually 5- or 6-membered rings. The core ring system is most usually fused 5- and 6-membered rings. The fused ring atoms may generally be any atom, usually carbon or hetero atoms, more usually carbon and nitrogen group atoms, and more usually still carbon and nitrogen. The number of carbon atoms in the core ring system is usually 7. The core ring system usually contains 2 hetero atoms, where the preferred hetero atom is nitrogen. Generally, one or more of the fused rings may be aromatic. When the core ring system is fused 5- and 6-membered rings, the core ring system is usually aromatic over both fused rings. The fused 5- and 6-membered ring system is most usually an indazole.

More particularly, lonidamine analogs for use according to the methods of the invention, and certain of the novel analogs provided by the invention, include analogs of the formula

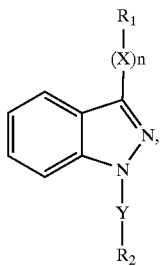

where $R_1$, $R_2$, X, Y, and n are generally as above or, in a preferred version, $R_2$ is —Cl, —Br, —I, or —CH$_3$, monosubstituted phenyl, substituted at the 2, 3, or 4 position; dichloro, dibromo, dimethyl, or chloro and methyl disubstituted phenyl, substituted at the 2 and 3 or 2 and 4 positions; or 2, 4, 5 trichlophenyl;

Y is —(CH$_2$)—; and n is zero, and $R_1$ is —COOH, —CONH$_2$, —CONHNH$_2$, —CONHN(CH$_3$)$_2$, —CH$_2$CH$_2$OH, —CH$_2$CH(OH)CH$_2$OH, or —CH$_2$(CH$_2$OH)$_2$; or n is one, $R_1$ is —COOH, and X is —CH=CH—.

In one embodiment, the lonidamine analog is a 1,3-substituted-indazole, such as a 1-halobenzyl-1H-indazole. In another embodiment, the lonidamine analog is a 3-substituted 1-benzyl-1H-indazole. In another embodiment, the lonidamine analog is a 1-substituted-indazole-3-carboxylic acid, such as a 1-halobenzyl-1H-indazole-3-carboxylic acid.

Bioisosteres. In addition, lonidamine analogs that may be used in the treatment methods of the invention include bioisosteres and pharmacophores of lonidamine and analogs described herein. Bioisosterism is a well-known tool for predicting the biological activity of compounds, based upon the premise that compounds with similar size, shape, and electron density can have similar biological activity. To form a bioisostere of a given molecule, one replaces one or more atoms or groups with known bioisosteric replacements for that atom or group. Known bioisosteric replacements include, for example, the interchangeability of —F, —OH, —NH$_2$, —Cl, and —CH$_3$; the interchangeability of —Br and -i-C$_3$H$_7$; the interchangeability of —I and -t-C$_4$H$_9$; the interchangeability of —O—, —S—, —NH—, —CH$_2$, and —Se—; the interchangeability of —N=, —CH=, and —P= (in cyclic or noncyclic moieties); the interchangeability of phenyl and pyridyl groups; the interchangeability of —C=C— and —S— (for example, benzene and thiophene); the interchangeability of an aromatic nitrogen ($R_1$—N($R_3$)—$R_2$) for an unsaturated carbon ($R_1$—C(=$R_3$)—$R_2$); and the interchangeability of —CO—, —SO—, and —SO$_2$—. These examples are not limiting on the range of bioisosteric equivalents and one of skill in the art will be able to identify other bioisosteric replacements known in the art. See, e.g., Patani and LaVoie, 1996; and Burger, 1991.

Pharmacophores. In addition to the lonidamine analogs described herein, lonidamine analogs that may be used in the methods of the invention can generally be any pharmacophore of lonidamine and the lonidamine analogs described above. Often a reasonable quantitative prediction of the binding ability of a known molecule can be made based on the spatial arrangement of a small number of atoms or functional groups in the molecule. Such an arrangement is called a pharmacophore, and once the pharmacophore or pharmacophores in a molecule have been identified, this information can be used to identify other molecules containing the same or similar pharmacophores. Such methods are well known to persons of ordinary skill in the art of medicinal chemistry, and as the structural information described in this application identifies the pharmacophore of lonidamine and the lonidamine analogs relevant to treatment of BPH, those of skill in the art can identify other LND analogs that comprise the pharmacophore and so are useful in treating BPH. An example of programs available to perform pharmacophore—related searches is the program 3D Pharmacophore search from the Chemical Computing Group (see http://www.chemcomp.com/fdept/prodinfo.htm).

A lonidamine analog of particular interest is tolnidamine (1-(4-chloro-2-methylbenzyl)-1H-indazole-3-carboxylic acid, AF 1923); see Ansari et al., 1998; Corsi et al., 1976. Tolnidamine (TND) differs from lonidamine by the presence of a methyl substituent, rather than a chlorine substituent, in position 2 of the benzyl group. Other analogs of lonidamine with biological activity have been described in the following publications: U.S. Pat. No. 3,895,026 entitled "Substituted 1-Benzyl-1H-Indazole-3-Carboxylic Acids and Derivatives Thereof;" Corsi et al., 1976, "1-Halobenzyl-1H-Indazole-3-Carboxylic Acids. A New Class of Antispermatogenic Agents," *Journal of Medicinal Chemistry* 19:778–83; Silvestrini, 1981, "Basic and Applied Research n the Study of Indazole Carboxylic Acids," *Chemotherapy* 27:9–20; Lobl et al., 1981, "Effects of Lonidamine (AF 1890) and its analogues on follicle-stimulating hormone, luteinizing hormone, testosterone and rat androgen binding protein concentrations in the rat and rhesus monkey," *Chemotherapy* 27:61–76; U.S. Pat. No. 6,001,865 entitled "3-Substituted 1-Benzyl-1H-Indazole Derivatives As Antifertility Agents"; and Cheng et al., 2001, "Two new male contraceptives exert their effects by depleting germ cells prematurely from the testis," *Biol Reprod.* 65:449–61, which describe AF-2364 and AF-2785 and other compounds (see FIG. 1).

Functional characteristics of lonidamine analogs. Lonidamine analogs suited for use in the invention are those that interfere with cellular energy metabolism of prostate epithelial cells when administered to a human, non-human primate, or other mammal. As is usual in the pharmaceutical arts, not every structural analog of a compound (e.g., lonidamine) is pharmacologically active. Active forms can be identified by routine screening of analogs for the activity of the parent compound. A variety of assays and tests can be used to assess pharmacological activity of lonidamine analogs, including in vitro assays, such as those described below and elsewhere herein, in vivo assays of prostate function (including citrate production and ATP production) in humans, non-human primates and other mammals, in vivo assays of prostate size in humans, non-human primates and other mammals, and/or clinical studies.

Apoptosis assay in cell lines. As shown in Example 3, lonidamine induces apoptosis in cell lines derived from human prostate cells. The induction of apoptosis is significantly greater in LNCaP cells (ATCC NO. CLR-1740), a prostate-derived cell line that is citrate-producing, than in PC3 cells (ATCC NO. CLR-1435), a prostate-derived cell line that is citrate-oxidizing, consistent with the susceptibility of the citrate-producing prostate cells to metabolic inhibitors such as lonidamine. In some embodiments of the invention in which a lonidamine analog is used for treatment or prevention of BPH or its manifestations, an analog with similar apoptosis-inducing activity is selected. Thus, in some embodiments of the invention, a lonidamine analog that induces apoptosis (enhances caspase 3 activity) in citrate-producing prostate cells, such as LNCaP cells, is administered to treat BPH. In some embodiments of the invention, a lonidamine analog that induces apoptosis in LNCaP cells to a significantly greater degree than in PC3 cells is administered to treat BPH. In some embodiments of the invention, the induction of apoptosis by the lonidamine analog is at least about 2-fold greater in LNCaP cells than in PC3 cells (and sometimes at least about 3-fold greater, at least about 4-fold greater, or at least about 10-fold greater) when assayed at the concentration of analog at which the difference in the level of apoptosis in the two cell lines is greatest (provided that the concentration of analog used in the assay is not greater than 1 mM).

Apoptosis assay in primary cell cultures. As shown in Example 3, lonidamine induces apoptosis in primary cultures of human prostate epithelial cells. The induction of apoptosis is significantly greater in primary cultures of prostate epithelial cells than in primary cultures of human prostate stromal cells, consistent with the susceptibility of citrate-producing prostate cells to metabolic inhibitors such as lonidamine. In some embodiments of the invention in which a lonidamine analog is administered for treatment or prevention of BPH or its manifestations, an analog with apoptosis-inducing activity similar to that of lonidamine is selected. Thus, in some embodiments of the invention, a lonidamine analog that induces apoptosis in prostate epithelial cells is administered to treat BPH. In some embodiments of the invention, a lonidamine analog that induces apoptosis in primary cultures of prostate epithelial cells to a significantly greater degree than in primary cultures of human prostate stromal cells is used. In some embodiments of the invention, the lonidamine analog does not significantly induce apoptosis in stromal cells. In some embodiments of the invention, induction of apoptosis by the lonidamine analog is at least 2-fold greater in epithelial cells than in stromal cells (and sometimes at least 4-fold greater, sometimes at 10-fold greater, and sometimes at least 20-fold greater) when assayed at the concentration of analog at which the difference in the level of apoptosis in the two cell lines is greatest (provided that the concentration of analog used in the assay is not greater than 1 mM).

HIF-1α expression assays. As shown in Example 2, lonidamine reduced HIF-1α expression/accumulation (measured in the nuclear fraction) in cells cultured under conditions of hypoxia by almost 2-fold at 200 micromolar and by more than 5 fold (i.e., more than 10-fold) at higher lonidamine concentrations. Thus, in some embodiments of the invention, an energolytic agent reduces HIF-1α expression (prevents HIF-1α accumulation) in LNCaP cells cultured under hypoxic conditions by at least about 2-fold, at least about 5-fold or at least about 10-fold compared to culture in the absence of lonidamine.

In the figures corresponding to Example 2, the effect of lonidamine on HIF-1α expression in prostate cells appears more pronounced in LNCaP cells than in PC3 cells cultured under hypoxic conditions (oxygen level <0.1%). Some lonidamine analogs useful for treatment of BPH according to the present invention may have a similar effect.

The results of these experiments do not definitively establish the mechanism or specificity of inhibition of HIF-1α by lonidamine. Lonidamine's effect on HIF-1α levels may be due entirely or in part to a general inhibition of protein synthesis, described as an activity of lonidamine by Floridi et al., 1985. Lonidamine's effect on HIF-1α levels could also be due entirely or in part to lonidamine's effect on oxygen utilization by mitochondria. Hagen et al., 2003, reported that HIF-1α is constitutively synthesized but degraded in the presence of oxygen. It is possible that, under hypoxic conditions, inhibition of mitochondrial respiration by lonidamine reduces oxygen consumption by mitochondria. This in turn could lead to enhanced activity of the oxygen-dependent enzyme, prolyl hydrolase, which plays a role in the HIF-1α degradation pathway.

Hexokinase activity. As discussed above, and without intending to be bound to any specific mechanism, the effects of lonidamine on the prostate may be mediated, at least in part, by its effects on mitochondria and mitochondrial hexokinase activity in secretory epithelial cells. Accordingly, some lonidamine analogs useful in the present invention have hexokinase inhibitory activity as great or greater than that of lonidamine. Assays for hexokinase activity are known in the art. See Fanciulli et al., 1996, and Floridi et al., 1981.

Antispermatogenic activity. Likewise, it is believed that the antispermatogenic activity of lonidamine results, at least in part, from energolytic effects in germ cells. Some lonidamine analogs useful in the present invention have antispermatogenic activity as great, or greater, than that of lonidamine. Assays for antispermatogenic activity are known in the art. See, e.g., Grima et al., 2001; Lohiya et al., 1991.

In addition to in vitro assays, energolytic agents can be evaluated in vivo for use in the methods of the invention. For example and without limitation, suitable assays include measurements of prostate function and activity.

In vivo measurements of prostate function. The effect of a compound on prostate function, and, in particular, on respiration, can be assessed by monitoring prostate tissue metabolism following administration of the compound. Some lonidamine analogs useful in the present invention will detectably reduce ATP, citrate, and/or lactate production by the prostate in animals (including humans, non-human primates and other mammals). ATP, citrate, and/or lactate levels can be monitored directly and/or indirectly in vivo using techniques of magnetic resonance spectroscopy (MRS) or other methods. See, for example, Narayan and Kurhanewicz, 1992; Kurhanewicz et al., 1991; Thomas et al., 1990, for MRS assays that can be applied for this purpose.

In vivo measurements of prostate size. The effect of a compound on prostate size can be assessed following administration of the compound using standard methods (for example, ultrasonography or digital rectal examination, for humans, and ultrasonography and/or comparison of organ weight in animals). Assays can be conducted in humans or, more usually, in healthy non-human animals or in monkey, dog, rat, or other animal models of BPH (see, Jeyaraj et al., 2000; Lee et al., 1998; Mariotti et al., 1982), Some lonidamine analogs useful in the present invention will detectably reduce prostate size in such assays and animal models.

Clinical trials. Clinical trials, such as that described for lonidamine in the Example, infra, can be used to assess the therapeutic effects of lonidamine analogs.

The activity of a lonidamine analog of interest in any of the aforementioned assays can be compared with that of lonidamine to provide guidance concerning dosage schedules for the compound, and other information. Generally, lonidamine analogs with greater biological activity per mg than lonidamine are of special interest.

4. Synthesis and Forms of Lonidamine and Lonidamine Analogs

Lonidamine and lonidamine analogs and derivatives can be prepared using by well known synthetic methods. Synthesis of lonidamine is described in U.S. Pat. No. 3,895,026 and Germany Patent No. 2,310,031. Synthesis of exemplary lonidamine analogs, including tolnidamine (TND), is described in the art (see, e.g., Corsi et al., 1976, "1-Halobenzyl-1H-Indazole-3-Carboxylic Acids. A New Class of Antispermatogenic Agents", *Journal of Medicinal Chemistry* 19:778–83; Cheng et al., 2001, "Two new male contraceptives exert their effects by depleting germ cells prematurely from the testis" *Biol Reprod.* 65:449–61; Silvestrini, 1981, "Basic and Applied Research in the Study of Indazole Carboxylic Acids" *Chemotherapy* 27:9–20; LobI et al., 1981, ""Effects of Lonidamine (AF 1890) and its analogues on follicle-stimulating hormone, luteinizing hormone, testosterone and rat androgen binding protein concentrations in the rat and rhesus monkey"" *Chemotherapy* 27:61–76; U.S. Pat. Nos. 3,895,026 and 6,001,865).). It will be appreciated, of course, that lonidamine analogs useful in the practice of the invention are not limited to those for which specific structures are provided in this disclosure or the cited references, and that the compounds described above are provided for illustration and not to limit the present invention. It also will be clear that lonidamine analogs useful in the methods of the present invention are not limited to those now described herein or elsewhere in the pharmaceutical and patent literature; the ordinarily skilled practitioner guided by the present disclosure can synthesize novel analogs suitable for use according to the present invention using routine methods of medicinal chemistry.

In certain embodiments, lonidamine or a lonidamine analog is provided in the form of a pharmaceutically acceptable salt. Pharmaceutically acceptable salts include addition salts with acids, as well as the salts with bases. Salts with bases are, for example, alkali metal or alkaline earth metal salts, such as sodium, potassium, calcium or magnesium salts, or ammonium salts, such as those with ammonia or suitable organic amines, e.g. diethylamine, di-(2-hydroxyethyl)-amine or tri-(2-hydroxyethyl)-amine. Suitable acids for the formation of acid addition salts are, for example, mineral acids, such as hydrochloric, hydrobromic, sulphuric or phosphoric acid, or organic acids, such as organic sulphonic acids, for example, benzenesulphonic, 4-toluenesulphonic or methanesulphonic acid, and organic carboxylic acids, such as acetic, lactic, palmitic, stearic, malic, maleic, fumaric, tartaric, ascorbic or citric acid.

Administration of ester, amide and prodrug derivatives of lonidamine and analogs is also contemplated in the practice of the present invention (see, e.g., U.S. Pat. No. 6,146,658, for general information regarding preparation of such derivatives from a compound of interest) as is administration of polymorphic forms, enantiomeric forms, tautomeric forms, solvates, hydrates, and the like.

5. Patients for Whom Administration of Lonidamine Provides Benefit

The present invention provides that administration of lonidamine to men afflicted with, or susceptible to, BPH can be therapeutically effective. Accordingly, in one aspect of the invention, lonidamine or a lonidamine analog is administered to a subject in need of treatment for BPH. In one embodiment, the subject in need of treatment is a human male who does not have cancer. As used herein, "a subject in need of treatment for BPH" is a man diagnosed with BPH. BPH is diagnosed using artknown methods and criteria. The most common test is the digital rectal examination in which a physician determines whether the prostate is of a normal size and firmness. Other diagnostic assays include a urine flow rate test, determination of post void residual urine volume (e.g., by palpitation of the abdomen, drainage of residual urine, x-ray urogramography, or ultrasonography), moderate or severe symptom scores on the American Urologic Association Symptom Index (AUASI; Barry et al., 1992) or. International Prostate Symptom Score (IPSS; Barry et al., 2001), and other tests known in the art.

Desired clinical results of treatment for BPH include, but are not limited to, alleviation or amelioration of one or more symptoms of BPH (see below), a reduction in prostate size (see below), a reduction in AUASI or IPSS scores compared to base line measurements prior to commencement of therapy (for example, by 3 points or more, such as by 5 points or more), AUASI or IPSS scores less than 8, a reduction in serum PSA by at least about 20%, such as by at least about 40%, a serum PSA less than 4, such as less than 2, improvement in urodynamic parameters, and other desired results that will be recognized by a treating physician as indicative of a reduction in severity of BPH in a subject. An assessment of the response to treatment can be made at any time following the first administration of the drug. For example, an assessment is made about 30 days, about 60 days, or about 90 days after beginning treatment. Alternatively, assessment can be made about 6, 12, 18, 24 or more months after beginning treatment. Alternatively, an assessment can be made less than about 30 days, about 30 days, about 60 days, or about 90 days after a course of treatment ends.

In a related aspect, lonidamine or a lonidamine analog is administered to a human subject exhibiting a symptom associated with BPH to reduce the frequency or severity of the symptom. As used herein, "a symptom associated with BPH" refers to any one or more of the following symptoms: (1) urinary urgency; (2) terminal dribbling of urine; (3) frequent urination; (4) nocturia; (5) a weak/slow stream of urine; (6) a sense of incomplete emptying; (7) intermittency; (8) straining; (9) dysuria; (10) hematuria; (11) acute urinary retention; (12) urinary tract infection; (13) incontinence. Administration of lonidamine or a lonidamine analog according to the methods of the invention typically results in a reduction in severity, or elimination, of one or more of these symptoms; usually results in either a reduction in severity of, or elimination of, all of these symptoms; and often results in elimination of all of these symptoms.

In another related aspect, lonidamine or a lonidamine analog is administered to reduce prostate size in a human subject in need of such reduction. As used herein, "a subject in need of reduction of prostate size" is a man having an enlarged prostate gland as determined by (1) imaging (e.g., ultrasonography, magnetic resonance imaging) or (2) one or more signs or symptoms resulting directly or indirectly from compression of the urethra by the prostate (e.g., including the symptoms of BPH discussed herein). A reduction in serum PSA (prostate specific antigen) is also a useful proxy for reduction of prostate volume. Although varying among individuals, enlarged prostates often exceed 30 grams, 40 grams, or 50 grams in size. The degree of reduction of prostate size will vary from subject to subject due to a number of factors, including the degree of enlargement at the time of onset of therapy, but will typically be a reduction of at least about 10% volume, more often at least about 25%, sometimes at least about 40%, sometimes at least about 50%, and sometimes an even greater than 50% reduction in prostate size is observed. This reduction can be determined by imaging or other methods. Serum PSA can also in some instances serve as a useful proxy for prostate volume.

In a related aspect, lonidamine or an analog is administered to a subject with a serum PSA level greater than 2 ng/ml. PSA is secreted only by the epithelial cells of the prostate. For men with BPH, higher PSA levels suggest a relatively higher ratio of epithelial cell proliferation to stromal cell proliferation than in men with lower PSA levels. The present invention provides a number of diagnostic methods suitable for use in determining patients who should respond favorably to treatment with lonidamine or an analog. Thus, lonidamine treatment can provide a therapeutic benefit to subjects with PSA levels greater than 2 ng/ml. Accordingly, subjects predicted to benefit significantly from treatment in accordance with the invention can be selected in a population of men with BPH by identifying subjects with a serum PSA value greater than 2 ng/ml. In one embodiment of the invention, the subject has a PSA level greater than about 4 ng/ml. Because higher PSA levels are also, and perhaps more closely, associated with prostate cancer than with BPH, in one embodiment, the subject selected for therapy with lonidamine or an analog has a PSA level less than about 10 ng/ml.

In one aspect of the invention, lonidamine or a lonidamine analog is administered to a subject who would benefit from prophylaxis of BPH. In one example, "a subject who would benefit from prophylaxis of BPH" is a man previously treated for BPH by surgery, transurethral microwave thermotherapy, transurethral needle ablation, transurethral electrovaporization, laser therapy, balloon dilatation, prostatic urethral stent, drug therapy, or other therapy and not currently diagnosed with or exhibiting symptoms of BPH. In another example, a subject who would benefit from prophylaxis of BPH is a man at increased risk for developing BPH due to age (e.g., men older than 40, older than 50, older than 60, or older than 70 years of age). In another example, a subject who would benefit from prophylaxis of BPH is a man who is asymptomatic, or has symptoms sufficiently mild so that no clear diagnosis of BPH can be made, but who has an elevated serum PSA level (e.g., PSA>2 ng/ml or, in some cases, >4 ng/ml).

Thus, in some cases, the subject to whom lonidamine is administered in accordance with the methods of the invention is a man who has previously been treated for BPH, while in other cases the subject is a man who has not previously been treated for BPH. Similarly, it will be clear that any references in this section to administration of lonidamine apply equally to administration of a biologically active lonidamine analog.

In one embodiment of the invention, the subject in need of treatment or prophylaxis for BPH either is not also under treatment for cancer or does not have cancer. In a related embodiment, the subject in need of treatment or prophylaxis for BPH has not been diagnosed as having cancer. In one embodiment, the subject in need of treatment or prophylaxis for BPH does not have cancer. In one embodiment, the subject in need of treatment has a cancer other than prostate cancer but does not have prostate cancer. As used herein, "cancer" has its ordinary medical meaning and refers to a malignancy (including head, neck, prostate and breast cancers, leukemias and lymphomas), generally characterized by clonality, autonomy, anaplasia, and metastasis (see Mendelsohn, 1991).

In one embodiment, the invention provides a method of treating BPH in a patient by administering lonidamine to the patient. In a related embodiment, the invention provides a method for treating BPH comprising (a) administering lonidamine to a patient diagnosed with BPH and (b) determining whether one or more manifestations of BPH are reduced in the patient. In one embodiment, the invention provides a method for treating BPH by (a) diagnosing BPH in a patient, (b) administering lonidamine to the patient and (c) determining whether one or more manifestations of BPH are reduced in said patient. In one embodiment, the invention provides a method of treating BPH in a patient by administering a lonidamine analog to the patient. In a related embodiment, the invention provides a method for treating BPH comprising (a) administering a lonidamine analog to a patient diagnosed with BPH and (b) determining whether one or more manifestations of BPH are reduced in the patient. In one embodiment, the invention provides a method for treating BPH by (a) diagnosing BPH in a patient, (b) administering a lonidamine analog to the patient and (c) determining whether one or more manifestations of BPH are reduced in said patient. In the foregoing embodiments, optionally the subject is not diagnosed with or under treatment for cancer; optionally has a PSA less than or equal to 2 ng/ml, optionally has a PSA greater than 2 ng/ml and less than 10 ng/ml.

In another aspect, the invention provides a method entailing (a) advertising the use of lonidamine, or a lonidamine analog, for treatment of BPH, and (b) selling lonidamine or a lonidamine analog to individuals for use for treatment of BPH. In one embodiment, the advertising makes reference to a trademark that identifies an lonidamine product and the lonidamine sold in step (b) is identified by the same trademark. It will be appreciated that the individuals to whom lonidamine is sold include corporate persons (corporations) and the like and "selling BPH to individuals for use for treatment of BPH" includes selling to, for example, a medical facility for distribution to patients for treatment of BPH.

In another embodiment, the invention provides a method of treating acute urinary retention in a human by administering lonidamine or a lonidamine analog to the human. Because acute urinary retention can be a symptom of BPH, this embodiment of the invention is applicable to any subject who suffers from acute urinary retention but has not been diagnosed as having BPH when lonidamine or a lonidamine analog is first administered.

6. Dose, Route, Schedule and Duration of Administration

A variety of routes and dosage schedules are appropriate for administration of lonidamine and lonidamine analogs according to the invention.

A preferred mode of delivery of lonidamine and lonidamine analogs to a patient is oral delivery. Preferred dosage forms for oral administration are pills, tablets, capsules, caplets, and the like, especially as formulated for sustained release. Other suitable forms for oral administration include troches, elixirs, suspensions, syrups, wafers, lozenges, and the like. Other modes of administration are also contemplated, including parenteral, inhalation spray, transdermal, rectal, intraprostatic injection (e.g., of lonidamine-containing microparticles) and other routes. lonidamine and lonidamine analogs may be formulated in suitable dosage unit formulations containing conventional non-toxic pharmaceutically acceptable carriers, adjuvants and vehicles appropriate for each route of administration. In one embodiment, the dosage form is the 150 mg unit dosage form marketed in Italy under the trade name DORIDAMINA.

The dose, schedule and duration of administration of lonidamine and lonidamine analogs will depend on a variety of factors, including the age, weight and health of the subject, the severity of BPH symptoms, if any, the subject's medical history, co-treatments, therapeutic goal (e.g., therapy or prophalaxis), the mode of administration of the drug, the formulation used, patient response to the drug, and the like. For illustration rather than limitation, three general categories of dosing for administration of lonidamine and lonidamine analogs can be described: high dosing, low dosing, and intermediate dosing. For reference, the standard lonidamine dose used for the treatment of the specific types of cancer for which lonidamine has been approved in a few countries in Europe is 150 mg po TID for about thirty days.

Low dosing. Low dosing is contemplated for the treatment and prophlaxis of BPH. Exemplary low doses of lonidamine or a lonidamine analog include, without limitation, doses in the range of 1–300 mg per day (total daily dosage), more often in the range of 5–300 mg/day, or sometimes in the range of 5–70 mg/day. Other exemplary low dose ranges include 1–25 mg/day, 20–45 mg/day, 40–65 mg/day, 40–70 mg/day, 50–100 mg/day, 50–200 mg/day, and 50–300 mg/day. In one embodiment, the low dose is 150 mg administered orally once per day; the Doridamina unit dose form can be used in this embodiment. In another embodiment, the low dose is 75 mg administered orally twice daily; the Doridamina unit dose form can be used in this embodiment by splitting it into two equal parts.

As noted, the daily dosages recommended herein may be divided for, for example, two-, three- or four-times per day administration. In one embodiment, the drug is formulated for administration once-per day. In one embodiment, the drug is formulated for administration less frequently than once per day. In another embodiment, a modified-release form of the drug is used.

Administration of low doses of lonidamine can be daily, every other day, five days on, two days off, and other schedules determined by the administering physician.

An advantage of low dose schedules of the invention is that this dose may be continued to be administered for weeks to months while limiting or eliminating the unwanted, albeit usually mild, side effects reported for higher doses of lonidamine (principally myalgia and testicular pain).

A low dose schedule can be used for therapy or prophalaxis. In one embodiment, a low dose form is used for a maintenance dose after a higher initial, priming or loading dose.

High dosing. In another embodiment, BPH is treated in accordance with the methods of the invention by administering to a BPH patient a higher dose of lonidamine or a lonidamine analog (usually for a shorter period of time than for low doses). Exemplary high doses include, without limitation, total daily doses greater than 0.5 g, such as doses in the range 0.5–5 g/day, 0.5–3 g/day, 0.5–1 g/day and 1–3 g/day, or higher doses. The daily dosages may be divided, for example, for two-, three- or four-time per day administration. In one embodiment, the drug is formulated for administration once-per day, or less frequently than once per day. In one embodiment, a modified-release form of the drug is used. Alternatively, a high dose can be administered on a one-time, once-a-week, once every two weeks, or once-a-month basis (e.g., 0.5–5 g/administration) or by other schedules to be determined by the administering physician.

A high dose schedule can be used for therapy or prophalaxis. In one embodiment, a high dose is administered in combination with, or following, a surgical or other non-drug treatment for BPH.

Intermediate dosing. In another embodiment, BPH is treated in accordance with the methods of the invention by administering lonidamine or a lonidamine analog to a BPH patient at a dose intermediate between a high dose and a low dose. Exemplary intermediate doses include, without limitation, doses greater than 300 and less than 500 mg/day, such as doses in the range >300–400 or 400<500 (e.g., 450 mg/day). The daily dosages may be divided, for example, for two-, three- or four-times per day administration. In an embodiment, the drug is formulated for administration once-per day or less frequently than once per day. In one embodiment, a modified-release form of the drug is used. Alternatively, this intermediate dose can be administered on a one-time, once-a-week, once every two weeks, or once-a-month basis (e.g., 300–500 mg/administration) or by other schedules to be determined by the administering physician. In one embodiment, the daily dosage is 150 mg of lonidamine or a lonidamine analog taken three times a day.

An intermediate dose schedule may be used for therapy or prophylaxis. In one embodiment, an intermediate dose is administered in combination with, or following, a surgical or other non-drug treatment for BPH.

It will be appreciated that these dosing schedules are for illustration and not limitation, and that a dosing schedule may change during a course of therapy based on, for example, a patient's response to the therapy or the use of a lonidamine analog that has an activity/dose profile significantly different from that of lonidamine.

Duration. In therapeutic and prophylactic applications, lonidamine or the lonidamine analog can be administered a single time or many times over periods as long as several months or years. In one embodiment of the invention, lonidamine or an analog is administered to a symptomatic (e.g., experiencing difficulty in urination) BPH patient only until the symptoms abate or disappear, and then treatment is stopped unless and until symptoms reappear. When symptoms reappear, administration of lonidamine or an analog is resumed. In another embodiment, treatment continues after symptoms disappear or are reduced to an acceptable target level, at least for a period of time, such as a week, two weeks, a month or several months. In another embodiment, the drug is administered to an asymptomatic subject to prevent the development or reoccurence of symptoms (i.e., prophylactically administered).

7. Treatment Combinations

Lonidamine and lonidamine analogs can be administered to a BPH patient in combination with other agents or procedures intended to treat BPH, ameliorate symptoms of BPH, potentiate the effects of the lonidamine or lonidamine analog, or provide other therapeutic benefit. Administration of an agent "in combination with" includes parallel administration (administration of both the agents to the patient over a period-of time, such as administration of lonidamine and tamsulosin on alternate days for one month), co-administration (in which the agents are administered at approximately the same time, e.g., within about a few minutes to a few hours of one another), and co-formulation (in which the agents are combined or compounded into a single dosage form suitable for oral or parenteral administration). Exemplary agents for administration in combination with lonidamine or lonidamine analogs include, but are not limited to, zinc, alpha-blockers, 5-alpha-reductase inhibitors, and plant extracts. Other agents for administration in combination with lonidamine or lonidamine analogs include other metabolic inhibitors, including but not limited to other hexokinase inhibitors and other inhibitors of glycolysis, including but not limited to 2-deoxy-D-glucose and an inhibitor, direct or indirect, of HIF-1α.

Zinc: As discussed above, high concentrations of zinc in the secretory epithelial cells of the prostate inhibit m-aconitase, increasing the dependence of that tissue on glycolysis for energy production. In accordance with the methods of the present invention, it may in some patients be beneficial to co-administer zinc (e.g., zinc chloride, zinc gluconate, zinc sulfate, zinc acetate, zinc aspatate, zinc citrate, zinc glycerate, zinc oxide, zinc picolinate, etc.) with a drug composition of the invention, to maximize the efficacy of the treatment. For example and not limitation, 15–300 mg/day zinc can be administered for this purpose, typically 30–50 mg/day are administered.

Alpha-Adrenergic-Blockers: Alpha-blockers alleviate some symptoms of BPH, without curing the underlying disease. These agents work by relaxing the muscles at the neck of the bladder and in the prostate, reducing the pressure on the urethra. Exemplary alpha-blockers include doxazosin (Cardura), terazosin (Hytrin), tamsulosin (Flomax), alfuzosin (Xatral), and prazosin (Hypovase). In one embodiment of the invention, an alpha blocker is administered in combination with lonidamine or a lonidamine analog to treat BPH. In another embodiment, the alpha-blocker is administered at a lower dosage (amount) or less frequently (e.g., alternate days rather than daily) than the "standard" dosage (the dosage that would be indicated for the subject in the absence of lonidamine administration) in combination with lonidamine or a lonidamine analog.

5-Alpha-Reductase Inhibitors: 5-alpha-reductase inhibitors inhibit the conversion of testosterone to dihydrotestosterone 2 (DHT), an androgen that contributes to prostate enlargement. An exemplary 5-alpha-reductase inhibitor is finasteride (Proscar). In one embodiment of the invention, a 5-alpha-reductase inhibitor is administered in combination with lonidamine to treat BPH. In another embodiment, the 5-alpha-reductase inhibitor is administered at a lower dosage (amount) or less frequently (e.g., alternate days rather than daily) than the "standard" dosage (the dosage that would be indicated for the subject in the absence of lonidamine administration) in combination with lonidamine (or an lonidamine analog).

Glycolytic and Mitochondrial Function Inhibitors: Glycolytic inhibitors, such as 2-deoxy-D-glucose and compounds that inhibit glucose transport, mitochondrial function inhibitors, mitochondrial poisons, and hexokinase inhibitors such as 3-bromopyruvate and its analogs can also be used in combination with lonidamine or a lonidamine analog to treat BPH. Such inhibitors are known in the art, and include those described in PCT patent publications WO 01/82926 published 8 Nov. 2001; U.S. Pat. Nos. 6,670,330; 6,218,435; 5,824,665; 5,652,273; and 5,643,883; U.S. patent application publication Nos. 2003/0072814; 2002/0077300; and 2002/0035071; and U.S. patent application Ser. No. 10/754, 239. Such inhibitors can be administered in combination with lonidamine or lonidamine analogs for therapeutic benefit in the treatment of BPH.

Plants: Saw Palmetto (*Serenoa repens*) or an extract thereof, or *Pygeum Africanum* or an extract thereof can be administered in combination with lonidamine or lonidamine analogs for therapeutic benefit in the treatment of BPH.

Procedures. In addition, lonidamine or a lonidamine analog may be administered in combination with, or prior to, procedures for treatment of BPH including surgery (transurethral resection of the prostate; transurethral incision of the prostate; or open prostatectomy), laser therapy, transurethral microwave thermotherapy, balloon dilatation, placement of a prostatic urethral stent, transurethral needle ablation, transurethral electrovaporization of the prostate, or other non-drug therapies.

8. Dosage Forms

Unit Dosage Forms. The compounds used in the methods of the present invention are formulated in compositions suitable for therapeutic administration. In one embodiment, the methods of the invention are practiced with lonidamine in the unit dosage form marketed as Doridamina (by ACRAF) in Italy. New dosage forms of lonidamine are also provided. For example, the present invention provides a unit dosage pharmaceutical formulation of lonidamine that is suitable for oral administration (including tablets, capsules, caplets, and pills) and contains, in various embodiments, an amount of lonidamine in a range bounded by a lower limit of (in mg) 1, 5, 10, and 50 and an upper limit of 10, 20, 40, 50, 70 and 100 (where the higher limit is in mg and greater than the lower limit) and is especially convenient for certain low dose schedules. In an other embodiment, the unit dosage form contains an amount of drug in a range bounded by a lower limit of (in mg) 200, 300, 500 or 1000 and an upper limit of 500, 1000, 3000 or 5000 (where the higher limit is greater than the lower limit) and is especially convenient for certain high dose schedules. In yet other embodiments, the formulation contains between 100 and 200 mg of compound (e.g., 150 mg), between 200 and 5000 mg, between 200 and 1000 mg, or between 500 and 1000 mg of the compound. Lonidamine analogs can be similarly formulated.

In addition to lonidamine and/or lonidamine analogs, solid unit dosage forms of the invention generally include a pharmaceutically acceptable carrier. As used herein, "pharmaceutically acceptable carrier" refers to a solid or liquid filler, diluent, or encapsulating substance, including for example excipients, fillers, binders, and other components commonly used in pharmaceutical preparations, including, but not limited to, those described below. Methods for formulation of drugs generally are well known in the art, and the descriptions herein are illustrative and not limiting. See, e.g., Ansel et al., 1999; Marshall, 1979.

Hydrophilic binders suitable for use in the formulations of the invention include copolyvidone (cross-linked polyvinylpyrrolidone), polyvinylpyrrolidone, polyethylene glycol, sucrose, dextrose, corn syrup, polysaccharides (including acacia, guar, and alginates), gelatin, and cellulose derivatives (including HPMC, HPC, and sodium carboxymethylcellulose).

Water-soluble diluents suitable for use in the formulations of the invention include sugars (lactose, sucrose, and dextrose), polysaccharides (dextrates and maltodextrin), polyols (mannitol, xylitol, and sorbitol), and cyclodextrins. Non-watersoluble diluents suitable for use in the formulations of the invention include calcium phosphate, calcium sulfate, starches, modified starches, and microcrystalline cellulose.

Surfactants suitable for use in the formulations of the invention include ionic and non-ionic surfactants or wetting agents such as ethoxylated castor oil, polyglycolyzed glycerides, acetylated monoglycerides, sorbitan fatty acid esters, poloxamers, polyoxyethylene sorbitan fatty acid esters, polyoxyethylene derivatives, monoglycerides or ethoxylated derivatives thereof, sodium lauryl sulfate, lecithins, alcohols, and phospholipids.

Disintegrants suitable for use in the formulations of the invention include starches, clays, celluloses, alginates, gums, cross-linked polymers (PVP, sodium carboxymethylcellulose), sodium starch glycolate, low-substituted hydroxypropyl cellulose, and soy polysaccharides. Preferred disintegrants include a modified cellulose gum such as cross-linked sodium carboxymethylcellulose.

Lubricants and glidants suitable for use in the formulations of the invention include talc, magnesium stearate, calcium stearate, stearic acid, colloidal silicon dioxide, magnesium carbonate, magnesium oxide, calcium silicate, microcrystalline cellulose, starches, mineral oil, waxes, glyceryl behenate, polyethylene glycol, sodium benzoate, sodium acetate, sodium chloride, sodium lauryl sulfate, sodium stearyl fumarate, and hydrogenated vegetable oils. Preferred lubricants include magnesium stearate and talc and combinations thereof.

The preferred range of total mass for the tablet or capsule may be from about 40 mg to 2 g, from about 100 mg to 1000 mg, and from about 300 mg to 750 mg.

Sustained Release Forms. In addition, the present invention provides unit dosage forms that are sustained release formulations of lonidamine or a lonidamine analog to allow once a day (or less) oral dosing, a frequency sometimes preferred by patients over multiple day dosing. Such sustained release formulations (including tablets, capsules, caplets and pills) of the invention usually contain between 1 mg and 3 g of the active compound, with various alternative embodiments including those described above for conventional oral unit doses, such as an amount of drug in a range bounded by a lower limit of (in mg) 1, 5,10, and 50 and an upper limit of 10, 20, 40, 50, 70 and 100 (where the higher limit is greater than the lower limit) and are especially convenient for certain low dose or intermediate dose schedules. In another embodiment, the unit dosage form contains an amount of drug in a range bounded by a lower limit of (in mg) 200, 300, 500, 750 or 1000 and an upper limit of 500, 1000, 2000, 3000 or 5000 (where the higher limit is greater than the lower limit).

In one embodiment, lonidamine or a lonidamine analog in the sustained release formulations (also called "modified" or "controlled" release forms) is released over a period of time greater than 6 hours, e.g., greater than 12 hours, after administration. In one embodiment, the sustained release formulation allows once a day dosing to achieve a pharmacodynamic profile therapeutically equivalent to dosing 150 mg of lonidamine three times a day.

Examples of sustained-release formulations for other drugs that can be modified in accordance with the teachings herein to be useful in the present invention are well known in the art, and are, for example, described in U.S. Pat. Nos. 5,968,551; 5,266,331; 4,970,075; 5,549,912; 5,478,577; 5,472,712; 5,356,467; 5,286,493; 6,294,195; 6,143,353; 6,143,322; 6,129,933; 6,103,261; 6,077,533; 5,958,459; and 5,672,360. Sustained-release formulations are also discussed in the scientific literature, e.g., in ORAL SUSTAINED RELEASE FORMULATIONS: DESIGN AND EVALUATION, edited by A. Yacobi and E. Halperin-Walega, Pergamon Press, 1988, which describes a variety of types of sustained-release dosage forms and drug release mechanisms, for example single unit (e.g., matrix tablets, coated tablets, capsules), multiple unit (e.g., granules, beads, micro-capsules), inert, insoluble matrix, hydrophilic gel matrix (e.g., bioadhesive, erodible, non-erodible), and ion-exchange resin sustained-release dosage forms.

In one embodiment, the present invention provides a method of treating BPH, by administering once daily to a patient in need of such treatment a sustained release tablet dosage form comprising a daily therapeutic dose of lonidamine from about 1 mg to 2 g in a hydrophilic matrix. The matrix can be, for example and without limitation, selected from the group consisting of hydroxypropylmethyl cellulose (by weight percent of about 20–40%), lactose (5–15%), microcrystalline cellulose (4–6%), and silicon dioxide (1–5%) having an average particle size ranging from 1–10 microns, often ranging from 2–5 microns, and most often ranging from about 2–3 microns.

Illustrative preferred sustained release formulations of the invention include formulations A and B in the table below.

|  | Formulation (weight percentage) | |
| --- | --- | --- |
|  | A | B |
| Lonidamine (milled) | 53.8 | 53.8 |
| HPMC (Methocel K15M, CR) | 8 | 30 |
| Methyl cellulose (Methocel, K100L, CR) | 18 | 0 |
| Anydrous lactose | 12.2 | 8.2 |
| Microcrystalline cellulose (Avicel PH101) | 5 | 5 |
| Silicon dioxide (1–10 micron; Syloid 244) | 3 | 3 |
| Total Table Weight (in grams) | 1 | 1 |

The sustained release formulations of the invention may be in the form of a compressed tablet containing an intimate mixture of lonidamine and a partially neutralized pH-dependent binder that controls the rate of drug dissolution in aqueous media across the range of pH in the stomach (typically ~2) and intestine (typically ~5.5).

Many materials known in the pharmaceutical art as "enteric" binders and coating agents have the desired pH dissolution properties suitable for use in the sustained formulations of the invention. These include phthalic acid derivatives such as the phthalic acid derivatives of vinyl polymers and copolymers, hydroxyalkylcellulose, alkylcelluloses, cellulose acetates, hydroxyalkylcellulose acetates, cellulose ethers, alkylcellulose acetates, and esters thereof, and polymers and copoloymers of lower alkyl acrylic acids and lower alkyl acrylates, and the partial esters thereof.

Preferred pH-dependent binder materials are methacrylic acid copolymers. Such a copolymer is commercially available from Rohm Pharma as Eudragit™ L-100-55 as a powder or L30D-55 as a 30% dispersion in water. Other pH-dependent binder materials which may be used alone or in combination include hydroxypropyl cellulose phthalate, hydroxypropyl methylcellulose phthalate, cellulose acetate phthalate, polyvinylacetate phthalate, polyvinylpyrrolidone phthalate, and the like. One or more pH-dependent binders are present in the sustained release oral dosage forms of the invention in an amount ranging from about 1 to 20 weight percent, or from 5 to 12 weight percent, or about 10%.

The pH-independent binders or viscosity enhancing agents contained in the sustained release formulations of the invention include substances such as hydroxypropyl methylcellulose, hydroxypropyl cellulose, methylcellulose, polyvinylpyrrolidone, neutral poly(meth)acrylate esters, and the like. The pH-independent binders are in an amount ranging from 1 to 10 weight percent or from 1 to 3 weight percent, or about 2%.

The sustained release formulations of the invention also contain in some embodiments one or more pharmaceutical excipients intimately mixed with the lonidamine and the pH-dependent binder, such as pH-independent binders or film-forming agent, starch, gelatin, sugars, carboxymethylcellulose, and the like, as well as other useful pharmaceutical diluents such as lactose, mannitol, dry starch, microcrystalline cellulose, and the like, and surface active agents such as polyoxyethylene sorbitan esters, sorbitan esters, and the like; and coloring agents and flavoring agents. Lubricants such as talc and magnesium stearate and tableting aids are also present.

The sustained release formulations of the invention include any of the commercially available polymers suitable for use in such formulations, including but not limited to cellulose, ethyl cellulose, methyl cellulose, carboxymethyl cellulose, hydroxypropylmethyl cellulose, hydroxypropylmethyl cellulose phthalate, hydroxypropyl cellulose, microcrystalline cellulose, sodium carboxymethyl cellulose, cellulose acetate phthalate, polyvinyl acetate phthalate, polyvinylpyrrolidone, polyethylene oxide, polyethylene glycol, zein, alginate, hypromellose phthalate, methacrylic acid copolymer, Crospovidone, silica aerogel, pregelatinized starch, corn starch, croscarmellose sodium, sodium starch glycolate, candelilla wax, paraffin wax, carnauba wax, montan glycol wax, white wax, Eudragit (polymethacrylic acid esters), Aquacoat (ethyl cellulose, cellulose acetate phthalate), Carbopol (acrylic acid polyalkeny polyether copolymer), and Macrogol (polyethylene glycol).

The sustained release formulations of the invention include formulations that are diffusion controlled, such as those that employ:

(a) a reservoir system in which the drug is encapsulated in a polymeric membrane, and water diffuses through the membrane to dissolve the drug, which then diffuses out of device;

(b) a monolithic (matrix) system in which the drug is suspended in a polymeric matrix and diffuses out through long pathways;

(c) microencapsulation and coated granule systems in which particles of drug (or particles of drug and polymer) as small as 1 micron are coated in a polymeric membrane, including embodiments in which particles coated with polymers with different release characteristics are delivered together in a capsule;

(d) solvent-activated systems, including (i) osmotically controlled devices (e.g. OROS) in which an osmotic agent and the drug are encapsulated in a semipermeable membrane, water is pulled into device due to osmotic gradient, and increased pressure drives drug out of device through a laser drilled hole; (ii) a hydrogel swelling system in which drug is dispersed in a polymer and/or a polymer is coated onto a particle of drug, and the polymer swells on contact with water (swelling is in some embodiments pH or enyzmatically controlled), allowing diffusion of drug out of the device; (iii) a microporous membrane system in which drug is encapsulated in a membrane that has a component that dissolves on contact with water (in some embodiments, dissolution is pH or enyzmatically controlled), leaving pores in the membrane through which the drug diffuses; and (iv) a wax matrix system in which the drug and an additional soluble component are dispersed in wax, such that, when water dissolves the component, diffusion of drug from the system is allowed; and (e) polymeric degradation systems, including (i) bulk degradation, in which drug is dispersed in polymeric matrix, and degradation occurs throughout the polymeric structure in a random fashion, allowing drug release; and (ii) surface erosion, in which drug is dispersed in polymeric matrix and delivered as the surface of the polymer erodes.

In one aspect, the invention provides a method for treating BPH by administering a unit dose oral pharmaceutical composition that is a sustained-release formulation containing an effective amount of lonidamine, such as described above, once per day.

9. Examples

Example 1

Clinical Trial

A Phase II randomized dose comparison study of lonidamine administration for the treatment of symptomatic benign prostatic hyperplasia is conducted. Patients are males 50 to 80 years of age with BPH confirmed by ultrasonography, a serum PSA >2, and no evidence of prostate cancer. Lonidamine (150 mg tablet; Doridamina formulation) is administered 150 mg p.o. TID (intermediate dosage) or QD (low dosage) 8 weeks. Patients receiving TID dosing take the compound 5 days on and 2 days off to aid compliance with the protocol.

Patients are assessed at baseline, day 30 and day 60 for prostate volume by ultrasonography, urine flow, AUASI score, PSA, adverse events, and serum chemistry to determine whether one of the two doses provides significantly greater benefit than the other dose and to measure the reduction in prostate size achieved by the therapy.

Example 2

Lonidamine Reduces Expression of HIF-1α in Prostate Cells

This example shows the effects of lonidamine treatment on HIF-1α expression in two cell lines derived from metastatic lesions of human prostate cancers. LNCaP is a citrate-producing cell (ATTC No. CRL-1740) while PC3 is citrate oxidizing cell (ATTC No.CRL-1435). See Franklin et al; 1995. Cells may be obtained from the American Type Culture Collection (ATCC), P.O.Box 1549, Manassas, Va. 20108 USA.

Figure 2:
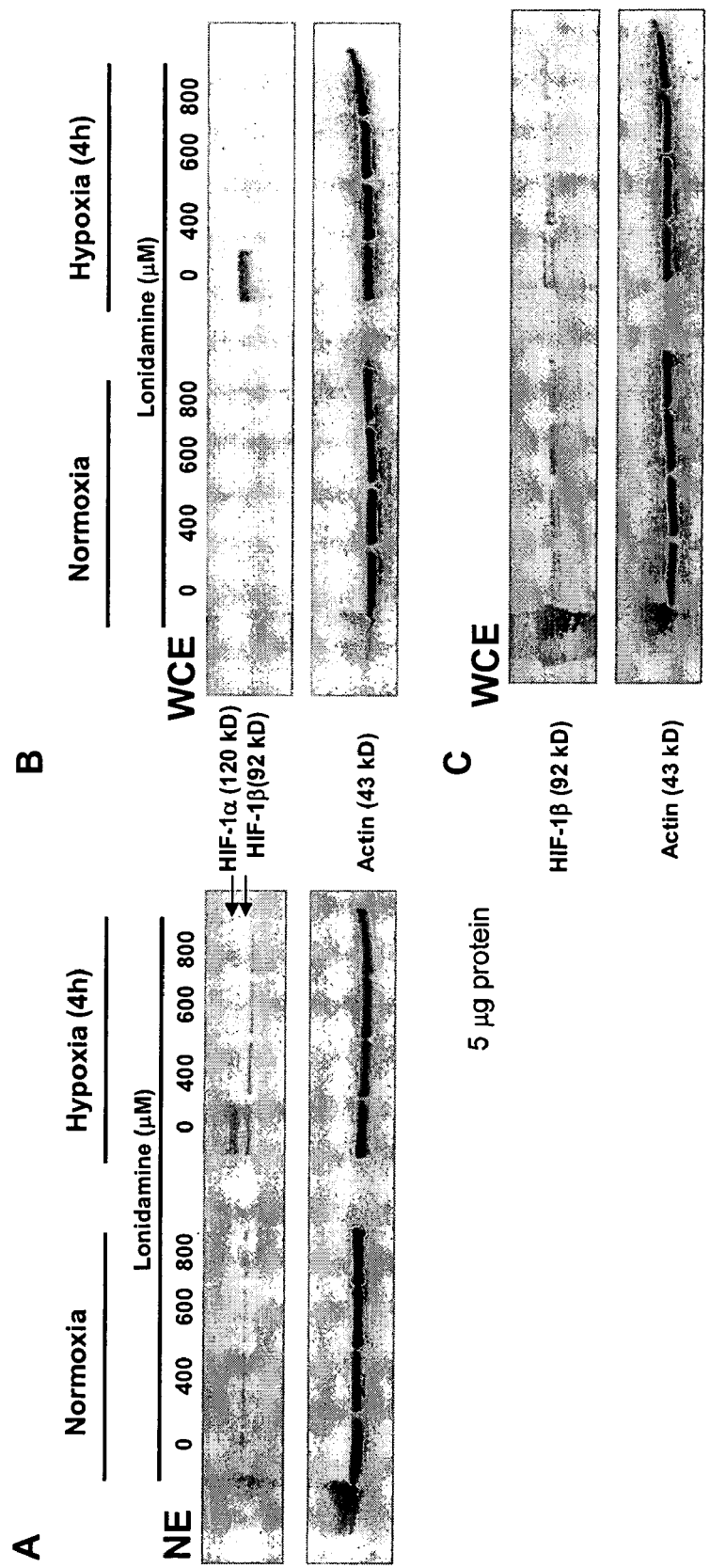
FIG. 2 shows the expression of HIF-1α in LNCaP cells under normoxic and hypoxic conditions and in the presence and absence of lonidamine.
Figure 3:
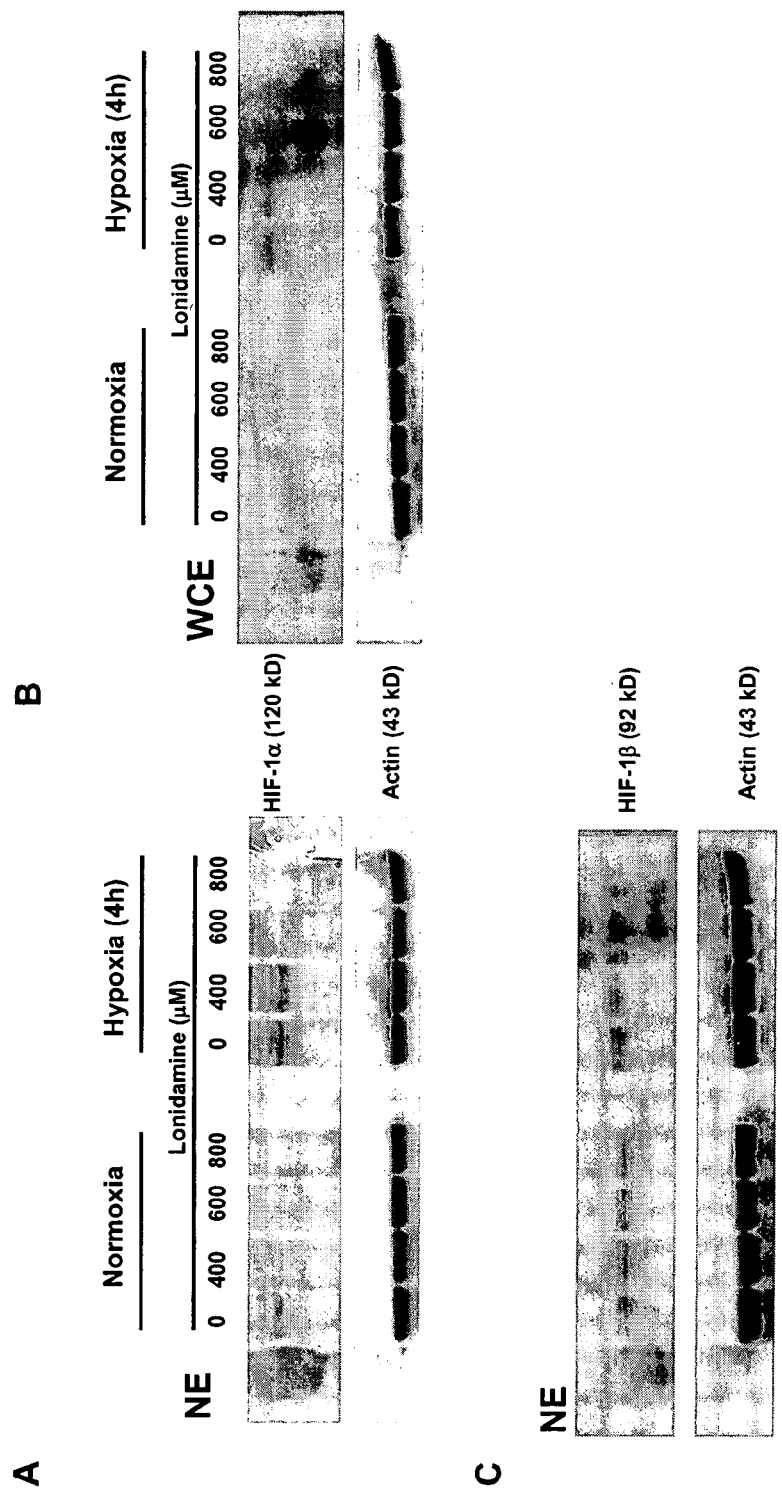
FIG. 3 shows the expression of HIF-1α in PC-3 cells under normoxic and hypoxic conditions and in the presence and absence of lonidamine.

As shown in FIGS. 2 and 3, lonidamine treatment reduced the level of HIF-1α protein detected in nuclear (NE) and whole-cell extract (WCE) preparations. The inhibition was dose-dependent, and observed under normoxic (PC3 cells only) and hypoxic conditions (LNCaP cells and PC3 cells). The lonidamine effect was specific to the HIF-1α subunit under the conditions tested and, except at 800 μM concentration, had no detectable inhibition under the conditions tested on the protein levels of actin, caspase 3, NF-κB, or IκBα. Lonidamine has, however, been reported to inhibit protein synthesis generally (see Floridi et al., supra), and the results presented herein should not be construed as definitive evidence that lonidamine is a specific inhibitor of HIF-1α or that lonidamine's therapeutic effect in the treatment of BPH is in whole or in part due to its inhibitory effect on the accumulation of HIF-1α in any cell type.

Methods: Cells were plated at a density of $5 \times 10^5$ cells into a dish, and then maintained in 37° C. incubator (5% $CO_2$) for 2 days. Prior to the assay, cells were rinsed twice with pre-warmed (37° C.) RPMI-1640 Medium (ATCC No. 30-2001; 10 mM HEPES; 1 mM sodium pyruvate; 2 mM L-glutamine; 4500 mg glucose/L; 1500 mg sodium bicarbonate/L). Cells were incubated with 2 ml culture medium in the absence or presence of lonidamine at different concentrations for 4 hours at 37° C. either under normoxia or hypoxia (oxygen level<0.1%). At the end of the incubation, the dish was placed on ice, and the cells were washed rapidly twice with cold PBS buffer (4° C.). For nuclear extracts, cells were lysed with buffer A (10 mM Tris, pH7.5; 1.5 mM $MgCl_2$; 10 mM KCl and protease inhibitors and buffer C (0.5 M NaCl; 20 mM Tris pH7.5; 1.5 mM $MgCl_2$; 20% glycerol and protease inhibitors), sequentially. The protease inhibitors used in the experiments were a cocktail of five protease inhibitors (500 mM AEBSF-HCl, 1 mg/ml Aprotinin, 1 mM E-64, 500 mM EDTA and 1 mM Leupeptin; Calbiochem NO 539131). For whole cell lysate, cells were lysed with 150 mM NaCl; 10 mM Tris ph7.5; 10 mM EDTA; 1% Triton X-100; 0.5% Deoxycholate, and protease inhibitors. The protein concentration was measured using a Bio-Rad protein assay. Equal amounts of protein were loaded on a SDS-PAGE gel. After transferring of the sample to PVDF membrane, the membrane was blocked with TBST containing 5% non-fat milk overnight at 4° C. Subsequently, the membrane was incubated with primary antibodies (HIF-1α, HIF-1β, and actin) and alkaline phosphatase-conjugated secondary antibody, for two hours each incubation. To detect the expression of caspase 3, NF-κB, P65 and IκBα, the membrane was blocked with TBST containing 5% non-fat milk for 1 h at room temperature, and the proteins were detected by incubation with the corresponding antibodies overnight at 4° C. and with the alkaline phosphatase-conjugated secondary antibody for 1 h. The specific protein was detected using a colorimetric substrate, and the intensity of each protein was quantified using an NIH image system.

Figure 7:
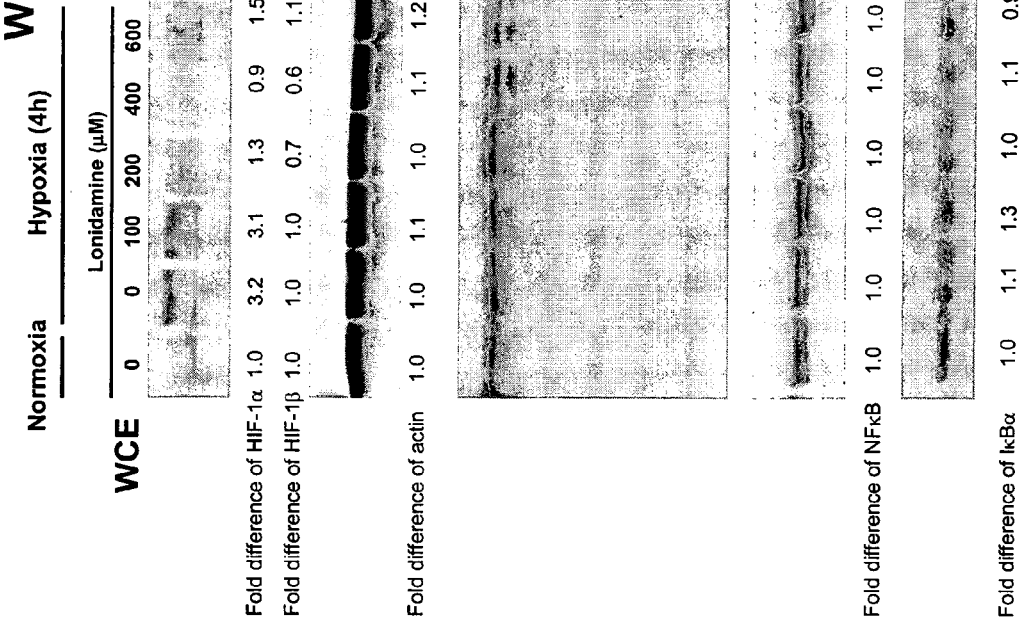
FIG. 7 shows the effect of 0–600 μM lonidamine on expression of HIF-1' and other proteins as determined in whole cell extracts from LNCaP cells cultured under hypoxic conditions.
Figure 8:
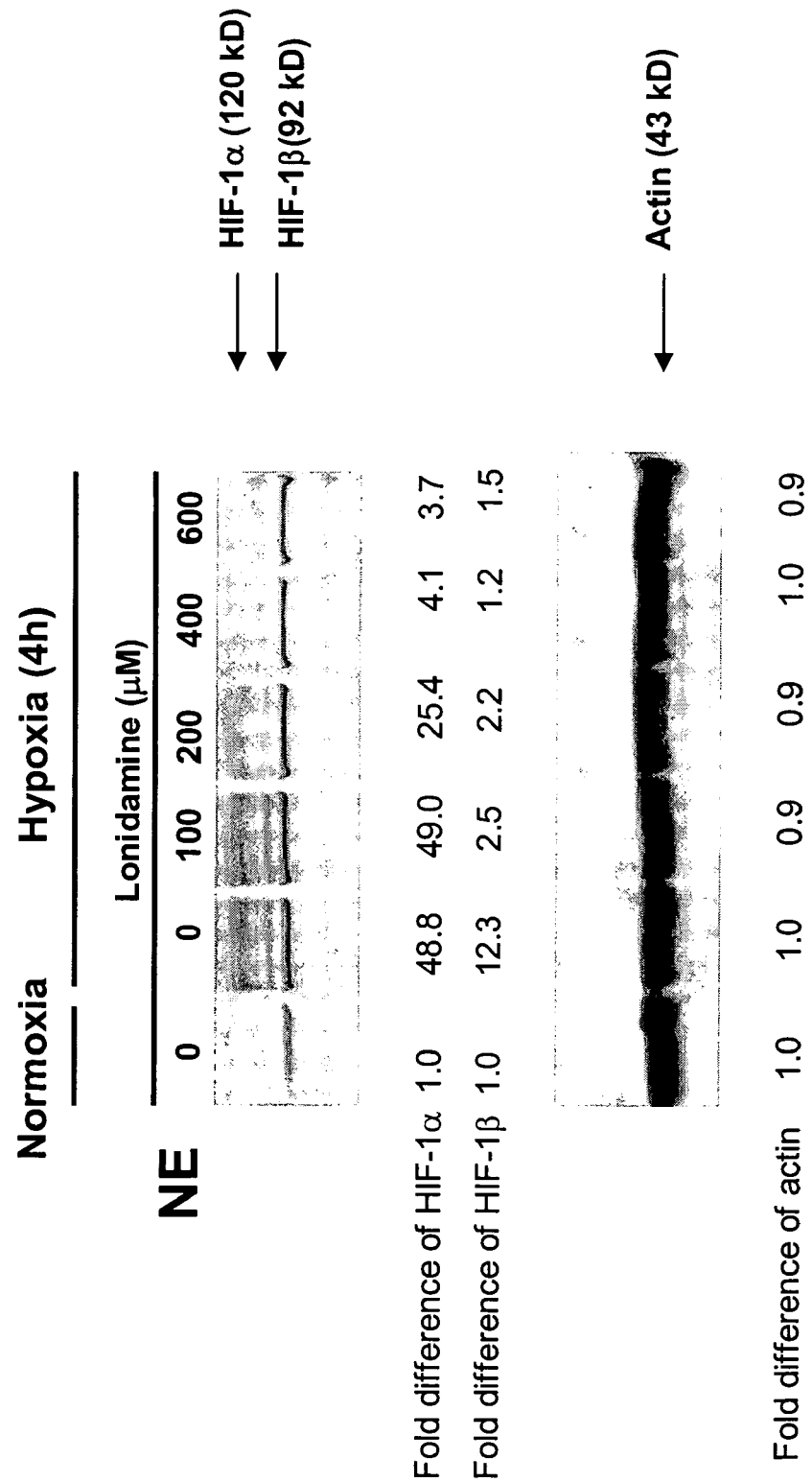
FIG. 8 shows the effect of 0–600 μM lonidamine on expression of HIF-1α and other proteins as determined in nuclear extracts from LNCaP cells cultured under hypoxic conditions.

In separate experiments carried out generally as above, the effect of 0–600 μM lonidamine on expression of HIF-1α and other proteins was determined in LNCaP whole cell extracts (FIG. 7) or nuclear extracts (FIG. 8) from cells cultured under hypoxic conditions.

Example 3

Lonidamine Induces Apoptosis in Citrate-Producing Cells

To determine whether apoptosis occurs in cells treated with lonidamine, the effect of lonidamine on cells producing citrate (LNCaP) and cells oxidizing citrate (PC3) was assessed. As shown in FIG. 4, lonidamine induced activation of caspase 3 in citrate-producing cells (LNCaP) to a much greater extent than in citrate-oxidizing cells (PC3). The activation of caspase3 is a time-dependent process (FIG. 5).

Figures 6A, 6B:
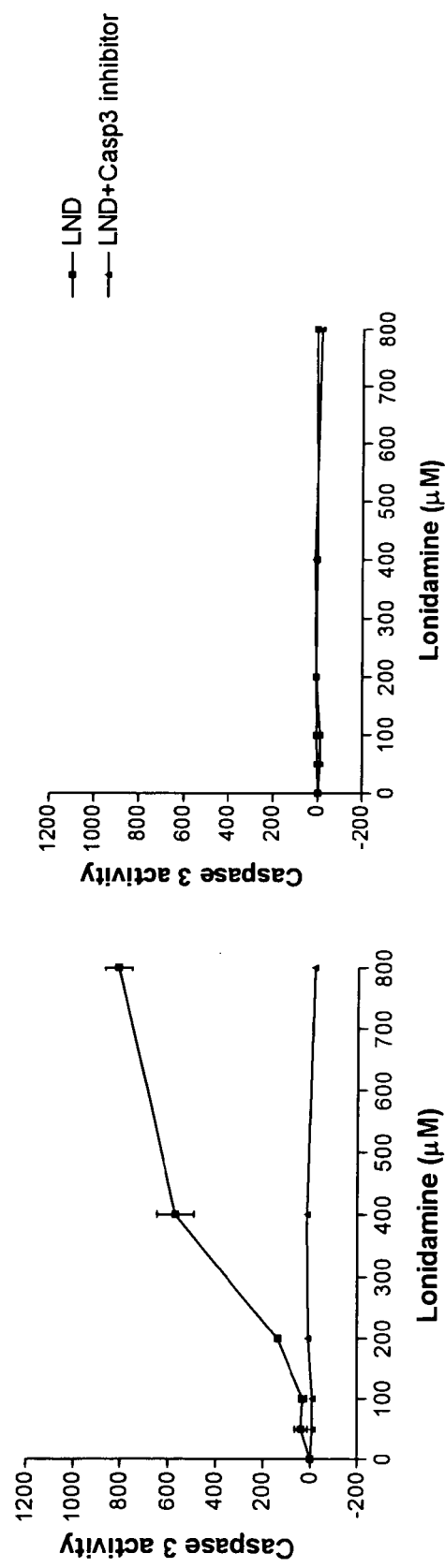
FIG. 6 shows lonidamine-induced apoptosis in prostate epithelial cells (FIG. 6A) and prostate stromal cells (FIG. 6B).

The effect of lonidamine was also examined in primary cultures of prostate epithelial cells (which accumulate citrate) or prostate stromal cells (which do not accumulate citrate). As shown in FIG. 6, lonidamine induced apoptosis only in prostate epithelial cells in a dose-dependent manner. In contrast, induction of apoptosis was not observed in prostate stromal cells after treatment with lonidamine.

Methods:

Immunoblotting: Immunoblotting was carried out as described in Example 2. To detect the expression of caspase 3, the membrane was blocked with TBST containing 5% non-fat milk for 1 h at room temperature, and caspase 3 protein was detected by incubation with caspase 3 antibody overnight at 4° C. and with the alkaline phosphatase-conjugated secondary antibody for 1 h. The specific protein was detected using colorimetric substrate, and the intensity of each protein was quantified using an NIH image system.

Primary Cell Cultures: Primary cultures of human prostate epithelial cells (Cambrex No. CC-2555) and human prostate stromal cells (Cambrex No. CC-2508) were obtained from Cambrex Bio Science Rockland, Inc. (191 Thomaston Street, Rockland, Me. 04841).

Apoptosis Assay: Cells were plated at a density of $2 \times 10^4$ cells per well in a 96 well plate, and then maintained in a 37° C. incubator (5% $CO_2$) for 16 h. Lonidamine was added into each well at different concentrations, and then incubated for 6 h at 37° C. To assess the caspase 3 activity, the homogeneous buffer and caspase 3 substrate (Promega No G7791; Promega Corporation, 2800 Woods Hollow Road, Madison Wis. USA 53711) were added into each well in the presence or absence of caspase 3 inhibitor (Promega No G5961). The fluorescence intensity of cleaved substrate was determined using a fluorescence plate reader at excitation 485 nm and emission 530 nm.

10. References Cited

Ansari et al., 1998, "Long-term sequelae of tolnidamine on male reproduction and general body metabolism in rabbits" Contraception 57:271–79.

Ansel et al., 1999, Pharmaceutical Dosage Forms and Drug Delivery Systems 7th ed. Lippincott Williams & Wilkins, Philadelphia: pp.1–562.

Barry et al., 1992, "Symptom index for benign prostatic hyperplasia" J Urol. 148:1549–57.

Barry et al., 2001, "Measuring the symptoms and health impact of benign prostatic hyperplasia and its treatments" BENIGN PROSTATIC HYPERPLASIA (5TH INTERNATIONAL CONSULTATION ON BPH). Health Publication, Ltd.

Barry et al., 2003, "Benign Prostatic Hyperplasic" in SCIENTIFIC AMERICAN MEDICINE, Dale and Federman Eds., WebMD Inc.

Burger, 1991, "Isosterism and Bioisosterism in Drug Design" A. Prog. Drug Res. 37:287–371.

Cheng et al., 2001, "Two new male contraceptives exert their effects by depleting germ cells prematurely from the testis" Biol Reprod. 65:449–61.

Corsi et al., 1976, "1-Halobenzyl-1H-Indazole-3-Carboxylic Acids. A New Class of Antispermatogenic Agents", Journal of Medicinal Chemistry 19:778–83.

Costello & Franklin, 2000, "The intermediary metabolism of the prostate: a key to understanding the pathogenesis and progression of prostate malignancy" *Oncology* 59:269–82

Costello et al., 1999, "Citrate in the diagnosis of prostate cancer" *Prostate* 38:237–45.

Costello et al., 2000, "Zinc causes a shift toward citrate at equilbrium of the maconitase reaction of prostate mitochondria" *J. Inorganic Biochemistry* 78:161–65.

Fanciulli et al., 1996, "Effect of the antitumor drug lonidamine on glucose metabolism of adriamycin-sensitive and -resistant human breast cancer cells" *Oncology Research* 3:111–120

Floridi et al., 1981, "Effect of lonidamine on the energy metabolism of Ehrlich ascites tumor cells" *Cancer Res.* 41:4661–6.

Franklin et al; 1995, "Regulation of citrate metabolism by androgen in the LNCaP human prostate carcinoma cell line." *Endocrine* 3:603–607

Gatto et al., 2002, "Recent studies on lonidamine, the lead compound of the antispermatogenic indazol-carboxylic acids" *Contraception* 65:277–78.

Grima et al., 2001; 2001, "Reversible inhibition of spermatogenesis in rats using a new male contraceptive, 1-(2, 4-dichlorobenzyl)-indazole-3-carbohydrazide" *Biol Reprod.* 64:1500–8.

Heywood et al., "Toxicological studies on 1-substituted-indazole-3-carboxylic acids." 1981, *Chemotherapy* 27:91–97.

Jeyaraj et al., 2000, "Effects of long-term administration of androgens and estrogen on rhesus monkey prostate: possible induction of benign prostatic hyperplasia" *J Androl.* 21:833–41.

Kaplan, 2000 "Correspondence re: M. Fanciulli et al., Energy metabolism of human LoVo colon carcinoma cells: correlation to drug resistance and influence of lonidamine." *Clin Cancer Res.* 6:4166–7.

Kurhanewicz et al., 1991, "$^{31}$P Spectroscopy of the human prostate gland in vivo using a transrectal probe" *Magnetic Resonance in Medicine* 22:404–13.

Kurhanewicz et al., 2000, *Radiol Clin North Am* 38:115–38.

Lee et al., 1998, "Chronology and urodynamic characterization of micturition in neurohormonally induced experimental prostate growth in the rat" *Neurourol Urodyn.* 17:55–69.

Lobl et al., 1981, "Effects of Lonidamine (AF 1890) and its analogues on follicle-stimulating hormone, luteinizing hormone, testosterone and rat androgen binding protein concentrations in the rat and rhesus monkey" *Chemotherapy* 27:61–76.

Lohiya et al, 1991, "Antispermatogenic effects of tolnidamine in langur (*Presbytis entellus*)" *Contraception* 43:485–96.

Mariotti et al., 1982, "Collagen and cellular proliferation in spontaneous canine benign prostatic hypertrophy" *J Urol.* 127:795–7.

Marshall, 1979."Solid Oral Dosage Forms," MODERN PHARMACEUTICS, Vol. 7, (Banker and Rhodes, editors), pp. 359–427.

Mendelsohn, 1991, "Principles of Neoplasia" in HARRISON'S PRINCIPLES OF INTERNAL MEDICINE, Wilson ed., McGraw-Hill, New York, p. 1576.

Narayan and Kurhanewicz, 1992, "Magnetic resonance spectroscopy in prostate disease: diagnostic possibilities and future developments." *Prostate Suppl.* 4:43–50.

Patani and LaVoie, 1996, "Bioisosterism: A Rational Approach in Drug Design" *Chem. Rev.* 96:3147–76.

Silvestrini et al., 1984, *Prog. Med. Chem.* 21, G. P. Ellis and G. B. West, Eds. (Elsevier Science Publishers, Amsterdam), p.111–35.

Silvestrini, 1981, "Basic and Applied Research n the Study of Indazole Carboxylic Acids" *Chemotherapy* 27:9–20.

Thomas et al., 1990, "$^1$H MR spectroscopy of normal and malignant human prostates in vivo." *Journal of Magnetic Resonance* 87:610–19.

Yacobi and Halperin-Walega, 1988, in Oral Sustained Release Formulations: Design. and Evaluation, Pergamon Press U.S. 2003/0072814 "Topical Pharmaceutical Composition for the Treatment of Warts".

U.S. 2002/0077300 "Screening Method for Cancer Therapeutics and Stable Antitumor Drug".

U.S. 2002/0035071 "Mimicking the Metabolic Effects of Caloric Restriction by Administration of Glucose Antimetabolites".

U.S. Pat. No. 3,895,026 "Substituted 1-benzyl-1H-indazole-3-carboxylic Acids and derivatives thereof".

U.S. Pat. No. 4,970,075 "Controlled Release Bases for Pharmaceuticals".

U.S. Pat. No. 5,266,331 "Controlled Release Oxycodone Compositions".

U.S. Pat. No. 5,286,493 "Stabilized Controlled Release Formulations Having Acrylic Polymer Coating".

U.S. Pat. No. 5,386,467 "Controlled Release Coatings Derived From Aqueous Dispersions of Zein".

U.S. Pat. No. 5,472,712 "Controlled Release Formulations Coated With Aqueous Dispersions of Ethylcellulose".

U.S. Pat. No. 5,478,577 "Methods of Treating Pain by Administering 24 Hour Oral Opioid Formulations Exhibiting Rapid Rate of Initial Rise of Plasma Drug Level".

U.S. Pat. No. 5,549,912 "Controlled Release Oxycodone Compositions".

U.S. Pat. No. 5,643,883 "Glucose-6-Phosphate Uptake Inhibitors and Novel Uses Thereof". U.S. Pat. No. 5,652,273 "Reduction of Hair Growth".

U.S. Pat. No. 5,672,360 "Method of Treating Pain by Administering 24 Hour Oral Opioid Formulations".

U.S. Pat. No. 5,824,665 "Reduction of Hair Growth".

U.S. Pat. No. 5,958,459 "Opioid Formulations Having Extended Controlled Released".

U.S. Pat. No. 5,968,551 "Orally Administrable Opioid Formulations Having Extended Duration of Effect".

U.S. Pat. No. 6,001,865 "3-substituted 1-benzyl-1H-indazole derivatives as antifertility agents".

U.S. Pat. No. 6,077,533 "Powder-Layered Oral Dosage Forms".

U.S. Pat. No. 6,103,261 "Opioid Formulations Having Extended Controlled Release".

U.S. Pat. No. 6,129,933 "Stabilized Controlled Release Substrate Having a Coating Derived From an Aqueous Dispersion of Hydrophobic Polymer".

U.S. Pat. No. 6,143,322 "Method of Treating Humans With Opioid Formulations Having Extended Controlled Release".

U.S. Pat. No. 6,143,353 "Controlled Release Formulations Coated With Aqueous Dispersions of Acrylic Polymers".

U.S. Pat. No. 6,146,658 "Prodrugs, their preparation and use as pharmaceuticals".

U.S. Pat. No. 6,218,435 "Reduction of Hair Growth".

U.S. Pat. No. 6,294,195 "Orally Administrable Opioid Formulations Having Extended Duration of Effect".

U.S. Pat. No. 6,670,330 "Cancer Chemotherapy With 2-Deoxy-D-Glucose".

WO 01/82926 "Manipulation of Oxidative Phosphorylation for Hypersensitizing Tumor Cells to Glycolytic Inhibitors".

Although the present invention has been described in detail with reference to specific embodiments, those of skill in the art will recognize that modifications and improvements are within the scope and spirit of the invention, as set forth in the claims which follow. All publications and patent documents (patents, published patent applications, and unpublished patent applications) cited herein are incorporated herein by reference as if each such publication or document was specifically and individually indicated to be incorporated herein by reference. Citation of publications and patent documents is not intended as an admission that any such document is pertinent prior art, nor does it constitute any admission as to the contents or date of the same. The invention having now been described by way of written description and example, those of skill in the art will recognize that the invention can be practiced in a variety of embodiments and that the foregoing description and examples are for purposes of illustration and not limitation of the following claims.

What is claimed is:

1. A method for treatment of benign prostatic hyperplasia (BPH) comprising administering a therapeutically effective amount of lonidamine to a human subject in need of such treatment.

2. The method of claim 1 comprising administering lonidamine to the subject at a dose of 150 mg administered orally once per day for one month.

3. The method of claim 1 wherein the subject is not being treated for cancer.

4. The method of claim 3 wherein the subject is not diagnosed as having cancer.

5. The method of claim 1 wherein the subject has a serum PSA greater than 2 ng/ml.

6. The method of claim 5 wherein the subject has a serum PSA less than 10 ng/ml.

7. The method of claim 1 wherein lonidamine is administered in combination with another treatment for BPH.

8. The method of claim 7 wherein the other treatment is: a) administration of an alpha-blocker; b) administration of a 5-alpha-reductase inhibitor; c) administration of zinc; or d) a surgical procedure.

9. The method of claim 1, wherein lonidamine is administered at least one day per week for at least 4 weeks.

10. The method of claim 1, wherein lonidamine is administered at least once daily for at least five days.

11. The method of claim 9 wherein the daily dose is in the range of 1 mg to 300 mg.

12. The method of claim 9 wherein the daily dose is between 300 mg and 5 grams.

13. The method of claim 9 wherein the daily dose is 150 mg p.o. TID.

14. The method of claim 1, wherein lonidamine is administered as a unit dose oral pharmaceutical composition that is a sustained-release formulation comprising from 1 mg to 2000 mg lonidamine.

15. The method of claim 1 wherein, when compared to a baseline prior to the initiation of treatment, the subject's a) AUASI or IPSS score is decreased by at least 3 points; b) prostate size has decreased by at least about 20%; and/or c) serum PSA levels have decreased by at least about 20%, when determined on or after 60 days after the initiation of treatment.

16. A method for treating BPH comprising (a) diagnosing BPH in a patient, (b) administering lonidamine to the patient and (c) determining whether one or more manifestations of BPH are reduced in said patient.

17. A method for treating BPH comprising (a) administering lonidamine to a patient diagnosed with BPH and (b) determining whether one or more manifestations of BPH are reduced in said patient.

18. The method of claim 11 wherein the daily dose is in the range of 5 mg to 70 mg.

19. The method of claim 10 wherein the daily dose is in the range of 1 mg to 300 mg.

20. The method of claim 19 wherein the daily dose is in the range of 5 mg to 70 mg.

21. A method for reducing a symptom associated with BPH comprising administering lonidamine to a human subject in need of such treatment, wherein the subject is not under treatment for cancer or diagnosed with cancer.

22. The method of claim 21, wherein lonidamine is administered at least once daily for at least five days.

23. The method of claim 22 wherein the daily dose is in the range of 1 mg to 300 mg.

24. The method of claim 23 wherein the daily dose is in the range of 5 mg to 70 mg.

* * * * *